US012622665B2

(12) United States Patent
Sattarivand et al.

(10) Patent No.: US 12,622,665 B2
(45) Date of Patent: May 12, 2026

(54) ADAPTIVE DUAL-ENERGY X-RAY IMAGING USING PRE-CALIBRATED WEIGHTING FACTORS

(71) Applicant: Dalhousie University, Halifax (CA)

(72) Inventors: Mike Sattarivand, Halifax (CA); Ivan Romadanov, Halifax (CA)

(73) Assignee: Dalhousie University, Halifax (CA)

( * ) Notice: Subject to any disclaimer, the term of this patent is extended or adjusted under 35 U.S.C. 154(b) by 171 days.

(21) Appl. No.: 18/450,341

(22) Filed: Aug. 15, 2023

(65) Prior Publication Data

US 2024/0041419 A1    Feb. 8, 2024

Related U.S. Application Data

(63) Continuation of application No. PCT/CA2022/050244, filed on Feb. 18, 2022.
(Continued)

(51) Int. Cl.
*A61B 6/50* (2024.01)
*A61B 6/00* (2006.01)
(Continued)

(52) U.S. Cl.
CPC ............ *A61B 6/5258* (2013.01); *A61B 6/482* (2013.01); *A61B 6/583* (2013.01); *G01T 1/17* (2013.01);
(Continued)

(58) Field of Classification Search
CPC ....... A61B 6/482; A61B 6/5258; A61B 6/583; G01T 1/17; G06T 5/20; G06T 5/50;
(Continued)

(56) References Cited

FOREIGN PATENT DOCUMENTS

WO        2019237179 A1    12/2019

OTHER PUBLICATIONS

Romadanov et al., "Adaptive noise reduction for dual-energy x-ray imaging based on spatial variations in beam attenuation", Dec. 4, 2020.
(Continued)

*Primary Examiner* — Mark R Gaworecki
(74) *Attorney, Agent, or Firm* — Todd A. Rattray; Oyen Wiggs Green & Mutala LLP

(57) ABSTRACT

Methods for adaptive dual-energy imaging comprise calibrating a fitting model and implementing the calibrated model. Calibrating the model comprises: acquiring high and low energy images of a step phantom, generating regions of interest with overlapping materials, and determining an average intensity for each region of interest in each of the images; and determining a model material cancellation weighting factor and a model noise cancellation weighting factor for each of a first material and a second material for each region of interest. The weighting factors are fit to a fitting model. Implementing the calibrated model comprises: acquiring high and low energy images of a subject and generating maps of a subject-specific material cancellation weighting factor and a subject-specific noise cancellation weighting factor according to the fitting model; and applying the maps of the subject-specific material cancellation weighting factor and the subject-specific noise cancellation weighting factor to the images of the subject.

21 Claims, 13 Drawing Sheets

Related U.S. Application Data

(60) Provisional application No. 63/151,552, filed on Feb. 19, 2021.

(51) Int. Cl.

| | |
|---|---|
| *A61B 6/58* | (2024.01) |
| *G01T 1/17* | (2006.01) |
| *G06T 5/20* | (2006.01) |
| *G06T 5/50* | (2006.01) |
| *G06T 5/70* | (2024.01) |
| *G06T 7/00* | (2017.01) |
| *G06V 10/22* | (2022.01) |
| *G16H 30/20* | (2018.01) |
| *G16H 30/40* | (2018.01) |
| *G16H 50/50* | (2018.01) |

(52) U.S. Cl.

CPC .................. *G06T 5/20* (2013.01); *G06T 5/50* (2013.01); *G06T 5/70* (2024.01); *G06T 7/0012* (2013.01); *G06V 10/22* (2022.01); *G16H 30/40* (2018.01); *G16H 50/50* (2018.01); *G06T 2207/10116* (2013.01); *G06T 2207/20224* (2013.01); *G06T 2207/30008* (2013.01); *G06V 2201/03* (2022.01)

(58) Field of Classification Search

CPC ...................... G06T 5/70; G06T 7/0012; G06T 2207/10116; G06T 2207/20224; G06T 2207/30008; G06V 10/22; G06V 2201/03; G16H 30/40; G16H 50/50

See application file for complete search history.

(56) References Cited

OTHER PUBLICATIONS

Haytmyradov et al., "Adaptive weighted log subtraction based on neural networks for markerless tumor tracking using dual-energy fluoroscopy", 2020.

Darvish-Molla et al., "Patient-specific pixel-based weighting factor dual-energy x-ray imaging system using a priori CT data", 2019.

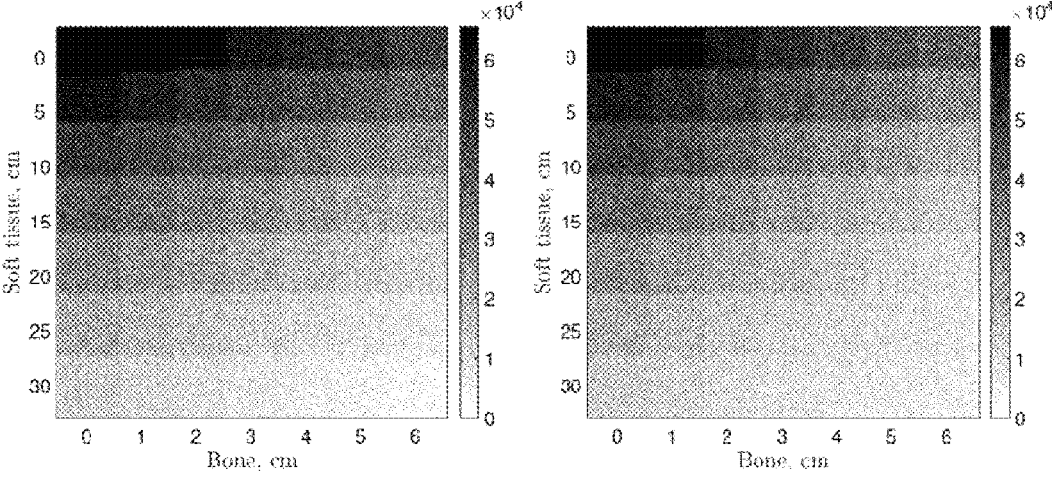
FIG. 2A                    FIG. 2B
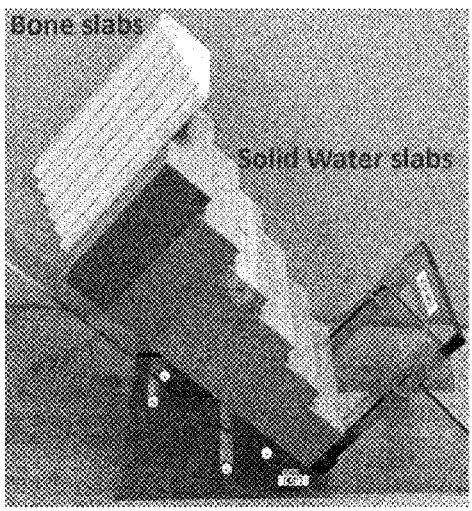
FIG. 2C

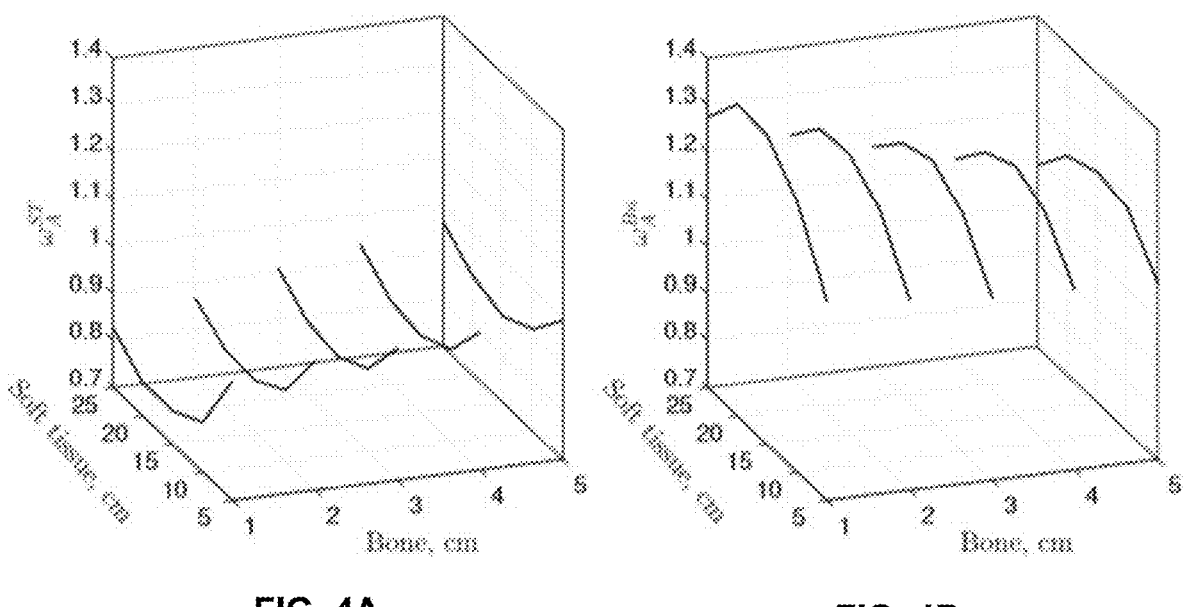
FIG. 4A                              FIG. 4B

ADAPTIVE DUAL-ENERGY X-RAY IMAGING USING PRE-CALIBRATED WEIGHTING FACTORS

CROSS-REFERENCE TO RELATED APPLICATIONS

This application is a continuation of Patent Cooperation Treaty (PCT) application No. PCT/CA2022/050244 having an international filing date of 18 Feb. 2022, which in turn claims priority from, and for the purposes of the United States of America the benefit under 35 U.S.C. § 119 of, U.S. application No. 63/151,552 filed 19 Feb. 2021. All of the applications in this paragraph are hereby incorporated herein by reference.

TECHNICAL FIELD

This invention pertains to dual-energy x-ray imaging. Some embodiments of the invention relate to dual-energy x-ray imaging methods which use a phantom for calibrating a model. Some embodiments relate to dual-energy x-ray imaging methods which use pre-calibrated models for generating x-ray images. Some embodiments of the invention relate to apparatus for dual energy x-ray imaging.

BACKGROUND

Projection x-ray imaging is commonly used in both diagnostic radiography (e.g. to diagnose a cancer lesion) and in image guided radiation therapy (IGRT) to enable precision therapy by identifying the tumor position. Image acquisition can be performed with a variety of techniques such as through the use of a linear accelerator (LINAC) or room mounted kV systems, which produce either volumetric (e.g. cone beam computed tomography) or planar images.

The benefits of x-ray imaging can often be limited by overlapping anatomical noise in the projection images, thus obscuring the region of interest (e.g. a tumor position). This may particularly be the case where the region of interest overlaps with bony anatomy. This results in reduced alignment and/or tracking accuracy. One technique aimed at solving this problem is dual-energy (DE) imaging.

DE imaging allows for material specific (bone or soft tissue) images to be obtained. DE imaging requires two radiographs obtained with x-ray beams of different spectra. Typically, this is achieved by acquiring images with different x-ray tube potentials. Such radiographs are referred to as high energy (HE) and low energy (LE) images. DE images are obtained by performing a logarithmic subtraction of individual energy images, where one of the images is multiplied by a weighting factor $\omega_{ST,Bn}$, which is also referred to as a material cancellation weighting factor (where ST and Bn stand for cancelling bone and soft-tissue, respectively). Mathematically, this can be expressed as:

$$\ln(DE)=\ln(HE)-\omega_{ST,Bn}\ln(LE) \tag{1}$$

Equation (1) provides for the complete cancellation of a material only with the assumption of a monoenergetic beam, usually referred to as simple log subtraction (SLS). In this case, the optimal weighting factor $\omega_{ST,Bn}$ is equal to the ratio of linear attenuation coefficients at different energies $\mu^{HE}/\mu^{LE}$ for bone or soft tissue. This weighting factor is assumed constant across the image.

Clinically used x-ray sources are polychromatic, which results in non-uniform beam hardening, due to different attenuation through anatomical structures of various thicknesses. Therefore, the weighting factors $\omega_{ST,Bn}$ are desirably optimized in a way to provide full cancellation of a signal of the undesired material (e.g. bone or soft tissue). However, due to the above-mentioned phenomena, it is impossible to completely negate the signal from the cancelled material if a constant weighting factor is used across the entire image. This results in a DE image with artifacts and reduced image quality.

Another important factor in DE images is noise. DE images typically have noise contributions from both HE and LE images. There are a variety of possible methods for reducing noise, such as simple smoothing of the high energy image and anti-correlated noise reduction (ACNR), for example.

ACNR utilizes the anti-correlation of noise on the material-specific images. For example, noise on the bone only image is anti-correlated to the noise on the soft tissue only image. Mathematically, the ACNR algorithm can be expressed as:

$$\ln(DE_{ACNR})=\ln(DE)-\omega_A(\ln(DE_C)^*h_{HPF}) \tag{2}$$

where DE is the DE image obtained using Equation (1), $\omega_A$ is the ACNR weighting factor, $DE_C$ is the complimentary material image (e.g. bone for soft-tissue and vice versa), and $*h_{HPF}$ denotes a convolution with a high-pass filter.

However, since the noise cancellation weighting factor $\omega_A$ is assumed to be constant across the image, this method does not take into account spatial variations of the noise arising from various quantum noise across the image due to different attenuating material thicknesses.

Methods have been proposed which involve applying spatially varying weighting factors based on a priori CT scans of patients in order to provide the material distribution of the imaged area. A priori CT scans are not always available and accurate image registration is time consuming and can be problematic if patient anatomy changes relative to the CT images.

Despite the work that has been done in the field of DE imaging to date there remains a need for DE imaging technologies which improve on the current state of the art.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

One aspect of the invention provides a method for processing x-ray images. The method comprises: obtaining higher energy (HE) and lower energy (LE) x-ray images of a subject and determining intensity values of pairs of corresponding aligned pixels of the HE and LE images respectively. For each of the pairs of corresponding pixels, the intensity values of the pair are used to determine first and second material cancellation weighting factors and a noise cancellation weighting factor. The method creates a first dual energy (DE) x-ray image by combining the HE and LE x-ray images by log subtraction of the intensity values of the pairs of corresponding aligned pixels of the HE and LE x-ray images using the first material subtraction weighting factor corresponding to the pair of corresponding aligned pixels to yield the logarithm of a corresponding pixel value for the first DE x-ray image. The method creates a second dual energy (DE) x-ray image complementary to the first DE x-ray image by combining the HE and LE x-ray images by log subtraction of the intensity values of the pairs of corresponding aligned pixels of the HE and LE x-ray images using the second material subtraction weighting factor corresponding to the pair of corresponding aligned pixels to yield the logarithm of a corresponding pixel value for the second DE x-ray image. The method processes pixels of the first DE x-ray image to reduce noise using the noise cancellation weighting factor corresponding to each of the pixels and the second DE x-ray image.

In some embodiments processing the pixels of the first DE x-ray image to reduce noise comprises generating a noise cancellation image by convolving a logarithm of the second DE x-ray image with a high pass filter and for each of the pixels of the first DE x-ray image subtracting rom the logarithm of the corresponding pixel value of the first DE x-ray image a corresponding pixel value of the noise cancellation image weighted by the corresponding noise cancellation weighting factor.

In some embodiments processing the pixels of the first DE x-ray image to reduce noise comprises, computing:

$$\ln(DE_{ACNR}) = \ln(DE) - \omega_A(\ln(DE_C) * h_{HPF})$$

where $DE_{ACNR}$ is an array of the pixel values of a noise-reduced version of the first DE x-ray image, DE is an array of the pixel values of the first DE x-ray image, $\omega_A$ is the corresponding noise cancellation weighting factor, $DE_C$ is an array of the pixel values of the second DE x-ray image and $*h_{HPF}$ denotes a convolution with a high-pass filter.

In some embodiments one of the first and second material cancellation weighting factors is a bone cancellation weighting factor and the other one of the first and second material cancellation weighting factors is a soft tissue cancellation weighting factor.

In some embodiments the method comprises applying dark field and/or flood field corrections to one or both of the HE and LE x-ray images.

In some embodiments using the intensity values of the pair to determine the first and second material cancellation weighting factors comprises inputting the intensity values of the pair into first and second fitted models which relate pairs of corresponding intensity values of the LE and HE x-ray images to the first and second material cancellation weighting factors respectively.

In some embodiments the first and second fitted models comprise first and second calibration functions that each take as arguments a pair of an intensity value from the LE x-ray image and a corresponding intensity value from the HE x-ray image and the method comprises receiving the first and second material cancellation weighting factors as outputs of the first and second calibration functions respectively.

In some embodiments the first and second fitted models are respectively embodied in first and second lookup tables wherein using the intensity values of the pair to determine the first and second material cancellation weighting factors comprises using the intensity values of the pair as keys for the first and second lookup tables and receiving the first and second material cancellation weighting factors as outputs of the first and second lookup tables respectively.

In some embodiments he first and second fitted models are obtained by: obtaining HE and LE x-ray images of a phantom comprising a plurality of different regions, each of the regions of the phantom comprising a first material, a second material or overlapping first and second overlapping materials; identifying the regions of the phantom in the HE and LE x-ray images of the phantom; determining an average intensity for each of the identified regions in each of the HE and LE x-ray images of the phantom; determining a model material cancellation weighting factor for each of the first material and the second material for each of the regions of the phantom; fitting the model material cancellation weighting factor for the first material for the regions of the phantom as a function of the average intensities of the HE and LE x-ray images of the phantom for the regions of the phantom to provide the first fitted model; and fitting the model material cancellation weighting factor for the second material for the regions of the phantom as a function of the average intensities of the HE and LE x-ray images of the phantom for the regions of the phantom to provide the second fitted model.

In some embodiments one of the first and second materials of the phantom is a bone mimicking material and the other one of the first and second materials of the phantom is a soft tissue mimicking material.

In some embodiments determining the model material cancellation weighting factor for each of the first and second materials is based on achieving a contrast to noise ratio (CNR) of zero between regions in which the first and second materials overlap and regions comprising only the first or second material respectively.

In some embodiments the phantom is a step phantom comprising slabs of soft tissue mimicking material and bone mimicking material wherein each of the regions has a corresponding thickness of the soft tissue mimicking material or a corresponding thickness of the bone mimicking material or a corresponding thickness of the soft tissue mimicking material or a corresponding thickness of the bone mimicking material.

In some embodiments using the intensity values of the pair to determine the noise cancellation weighting factor comprises inputting the intensity values of the pair into a first fitted noise cancellation model which relates pairs of corresponding intensity values of the LE and HE x-ray images to the noise cancellation weighting factor.

In some embodiments the first fitted noise cancellation model comprises a first noise cancellation function that takes as arguments a pair of an intensity value from the LE x-ray image and a corresponding intensity value from the HE x-ray image and the method comprises receiving the noise cancellation weighting factor as an output of the first noise cancellation calibration function.

In some embodiments the first fitted noise cancellation model is embodied in a first noise cancellation lookup table and wherein using the intensity values of the pair to determine the noise cancellation weighting factor comprises using the intensity values of the pair as keys for the first noise cancellation lookup table and receiving the noise cancellation weighting factor as an outputs of the first noise cancellation lookup table.

In some embodiments the first fitted noise cancellation model is obtained by: obtaining HE and LE x-ray images of a phantom comprising a plurality of different regions, each of the regions of the phantom comprising a first material, a second material or both the first and second materials overlapping; identifying the regions of the phantom in the HE and LE x-ray images of the phantom; determining an average intensity for each of the identified regions in each of the HE and LE x-ray images of the phantom; determining a first model noise cancellation weighting factor corresponding to the first material for each of the regions of the phantom by the ACNR method; and fitting the first model material cancellation weighting factors for the first material for the regions of the phantom as a function of the average intensities of the HE and LE x-ray images of the phantom for the regions of the phantom to provide the first fitted noise cancellation model.

In some embodiments the method further comprises providing a second fitted noise cancellation model, the second fitted noise cancellation model being generated by: determining a second model noise cancellation weighting factor corresponding to the second material for each of the regions of the phantom by the ACNR method; and fitting the second model noise cancellation weighting factors for the second material for the regions of the phantom as a function of the average intensities of the HE and LE x-ray images of the phantom for the regions of the phantom to provide the second fitted noise cancellation model.

In some embodiments determining the first model noise cancellation weighting factors comprises generating a first dual energy (DE) x-ray image of the phantom by combining the HE and LE x-ray images of the phantom by log subtraction of the intensity values of the pairs of corresponding aligned pixels of the HE and LE x-ray images using the first material cancellation weighting factor corresponding to the pair of corresponding aligned pixels to yield the logarithm of a corresponding pixel value for the first DE x-ray image of the phantom and selecting values for the first model noise cancellation weighting factors to maximize the signal-to-noise (SNR) ratio for each region of the phantom in the first DE x-ray image of the phantom.

In some embodiments phantom is a step phantom comprising slabs of soft tissue mimicking material and bone mimicking material wherein each of the regions has a corresponding thickness of the soft tissue mimicking material or a corresponding thickness of the bone mimicking material or a corresponding thickness of the soft tissue mimicking material or a corresponding thickness of the bone mimicking material.

In some embodiments acquiring the HE x-ray image comprises using a beam energy of about 140 kVp, In some embodiments acquiring the LE x-ray image comprises using a beam energy of about 60 kVp.

Another aspect of the invention provides a method for dual energy x-ray imaging. The method comprises obtaining higher energy (HE) and lower energy (LE) x-ray images of a subject and based on pixel intensities of the HE and LE x-ray images, generating patient specific maps of material cancellation $\omega_{ST,Bn}$ and noise cancellation $$\omega_A^{ST,Bn}$$

weighting factors and combining the LE and HE x-ray images to yield a dual-energy (DE) x-ray image using the material cancellation $\omega_{ST,Bn}$ and noise cancellation $$\omega_A^{ST,Bn}$$

weighting factors.

6

In some embodiments combining the LE and HE x-ray images comprises log subtraction.

In some embodiments the log subtraction comprises:

$$\ln(DE)=\ln(HE)-\omega_{ST,Bn}\ln(LE)$$

where DE is an array of the pixel values of the DE x-ray image, HE is an array of the pixel values of the HE x-ray image, LE is an array of the pixel values of the LE x-ray image and, $\theta_{ST,BnA}$ is the corresponding material cancellation weighting factor, ST indicates soft tissue, Bn indicates bone.

Another aspect of the invention provides a method for adaptive dual-energy imaging. The method comprises: calibrating first and second fitted models respectively for first and second material cancellation weighting factors, wherein calibrating the first and second fitted models comprises: acquiring higher energy (HE) and lower energy (LE) x-ray images of a step phantom comprising a first material and a second material; finding regions of interest in the HE and LE x-ray images wherein the regions of interest correspond portions of the step phantom in which the first and second materials overlap; determining an average intensity for each region of interest in each of the HE and LE x-ray images; determining a model material cancellation weighting factor for each of the first material and a second material for each of the regions of interest; and fitting the model material cancellation weighting factors for the first and second materials respectively as a function of the signal intensities of the HE and LE x-ray images to provide the first and second fitted models.

In some embodiments the method comprises determining a model noise cancellation weighting factor for each of the first and second materials for each of the regions of interest; and fitting the model noise cancellation weighting factors for the first and second materials respectively to first and second noise cancellation fitted models.

In some embodiments the method comprises acquiring HE and LE x-ray images of a subject; generating a material cancellation map of subject-specific location-specific material cancellation weighting factors for the subject by for each of a plurality of locations using corresponding intensity values of the HE and LE x-ray images of the subject to obtain a corresponding material cancellation weighting factor from one of the first and second fitted models; and applying the material cancellation map to combine the HE and LE images of the subject into a DE image of the subject.

In some embodiments the method comprises: acquiring HE and LE x-ray images of a subject; generating a material cancellation map of subject-specific location-specific material cancellation weighting factors for the subject by for each of a plurality of locations using corresponding intensity values of the HE and LE x-ray images of the subject to obtain a corresponding material cancellation weighting factor from one of the first and second fitted models; applying the material cancellation map to combine the HE and LE x-ray images of the subject into a DE x-ray image of the subject; generating a noise cancellation map of subject-specific noise cancellation weighting factors from one of the first and second noise cancellation fitted models for each of a plurality of locations in the DE x-ray image of the subject; and applying the noise cancellation map to the DE x-ray image of the subject.

In some embodiments the method comprises determining the model noise cancellation weighting factors for the first and second materials based on maximizing a signal to noise ratio (SNR).

In some embodiments applying the material cancellation map comprises performing log subtraction of the HE and LE images of the subject to produce the DE x-ray image of the subject and wherein applying the noise cancellation map comprises performing ACNR on the DE x-ray image of the subject.

In some embodiments determining the model material cancellation weighting factor for each of the first and second materials is based on achieving a CNR of zero between regions of overlapping first and second materials and regions comprising only first and second materials, respectively.

Another aspect of the invention provides apparatus for dual energy (DE) x-ray imaging comprising a data processor configured by computer executable instructions to perform a method as described above or anywhere else herein.

Another aspect of the invention provides apparatus for dual energy (DE) x-ray imaging comprising: first and second fitted material cancellation models respectively corresponding to first and second materials, each of the first and second fitted material cancellation models comprising an input for receiving an intensity value for a pixel of a higher energy (HE) x-ray image and an input for receiving an intensity value for a pixel of a lower energy (LE) x-ray image and configured to output a material cancellation weighting factor corresponding to intensity values presented at the inputs; and a data processor. The data processor is configured to: process higher energy (HE) and lower energy (LE) x-ray images of a subject to obtain intensity values of pairs of corresponding aligned pixels of the HE and LE images respectively, for each of the pairs of corresponding pixels, using the intensity values of the pair as inputs to each of the first and second fitted material cancellation models to obtain corresponding first and second material cancellation weighting factors; and create a first dual energy (DE) x-ray image by combining the HE and LE x-ray images by log subtraction of the intensity values of the pairs of corresponding aligned pixels of the HE and LE x-ray images using the first material cancellation weighting factor corresponding to the pair of corresponding aligned pixels to yield the logarithm of a corresponding pixel value for the first DE x-ray image; and create a second dual energy (DE) x-ray image complementary to the first DE x-ray image by combining the HE and LE x-ray images by log subtraction of the intensity values of the pairs of corresponding aligned pixels of the HE and LE x-ray images using the second material cancellation weighting factor corresponding to the pair of corresponding aligned pixels to yield the logarithm of a corresponding pixel value for the second DE x-ray image.

In some embodiments the apparatus further comprises: first and second fitted noise cancellation models respectively corresponding to the first and second materials, each of the first and second fitted noise cancellation models comprising an input for receiving an intensity value for a pixel of the higher energy (HE) x-ray image and an input for receiving an intensity value for a pixel of the lower energy (LE) x-ray image and configured to output a noise cancellation weighting factor corresponding to intensity values presented at the inputs. The processor is further configured to: for each of the pairs of corresponding pixels, using the intensity values of the pair as inputs to one of the first and second fitted noise cancellation models to obtain a corresponding noise cancellation weighting factor; and process pixels of the first DE x-ray image to reduce noise using the corresponding noise cancellation weighting factors.

Another aspect of the invention provides a computer program product comprising a tangible medium storing machine readable, machine executable instructions that, when executed by a data processor cause the data processor to execute a method according to any of the above methods or any other methods described herein.

Another aspect of the invention provides apparatus comprising new and inventive feature, combination of features or subcombination of features as described herein.

Another aspect of the invention provides methods comprising any new and inventive step, act, combination of steps and/or acts or subcombination of steps and/or acts as described herein.

Another aspect of the invention provides a method for adaptive dual-energy imaging. The method comprises calibrating fitting models and implementing the calibrated models. Calibrating a fitting model may comprise acquiring high energy and low energy images of a step phantom, generating regions of interest with overlapping materials, and determining an average intensity for each region of interest in each of the high energy and low energy images. Calibrating the fitting model may further comprise determining a model material cancellation weighting factor for each of a first material and a second material for each of the regions of interest. The material cancellation weighting factor is fit to a first fitting model as a function of the signal intensities of the high energy and low energy images. Implementing the fitting models comprises acquiring high energy and low energy images of a subject and generating a material cancellation map of subject-specific material cancellation weighting factors for each region of interest in the high and low energy images of the subject according to the first fitting model. Implementing the fitting models further comprises applying the material cancellation map of the subject material cancellation weighting factor to the high and low energy images of the subject.

In some embodiments, the method comprises determining a model noise cancellation weighting factor for each of the first and second materials for each of the regions of interest and fitting the model noise cancellation weighting factors to a second fitting model. Implementing the fitting models may comprise generating a noise cancellation map of subject-specific noise cancellation weighting factors for each region of interest in the high energy and low energy images of the subject according to the second fitting model. Implementing the fitting models may further comprise applying the noise cancellation map to the high energy and low energy images of the subject.

In some embodiments, determining the model noise cancellation weighting factors for each of the first and second materials is based on maximizing an SNR ratio when a material cancellation weighting factor is selected to cancel second and first materials, respectively. In some embodiments, applying the material cancellation map comprises performing log subtraction of the high energy and low energy images to produce a dual-energy image and wherein applying the noise cancellation map comprises performing ACNR on the dual-energy image.

In some embodiments, determining the model material cancellation weighting factor for each of the first and second materials is based on achieving a CNR of zero between regions of overlapping first and second materials and regions comprising only first and second materials, respectively.

In addition to the exemplary aspects and embodiments described above, further aspects and embodiments will become apparent by reference to the drawings and by study of the following detailed descriptions.

It is emphasized that the invention relates to all combinations of the above features, even if these are recited in different claims.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

FIGS. 2A and 2B are projection images of a calibration step phantom. FIG. 2C shows an example step phantom set up.

FIGS. 4A and 4B show graphs of soft tissue and bone noise cancellation weighting factors for different material thicknesses, respectively.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Figure 1:
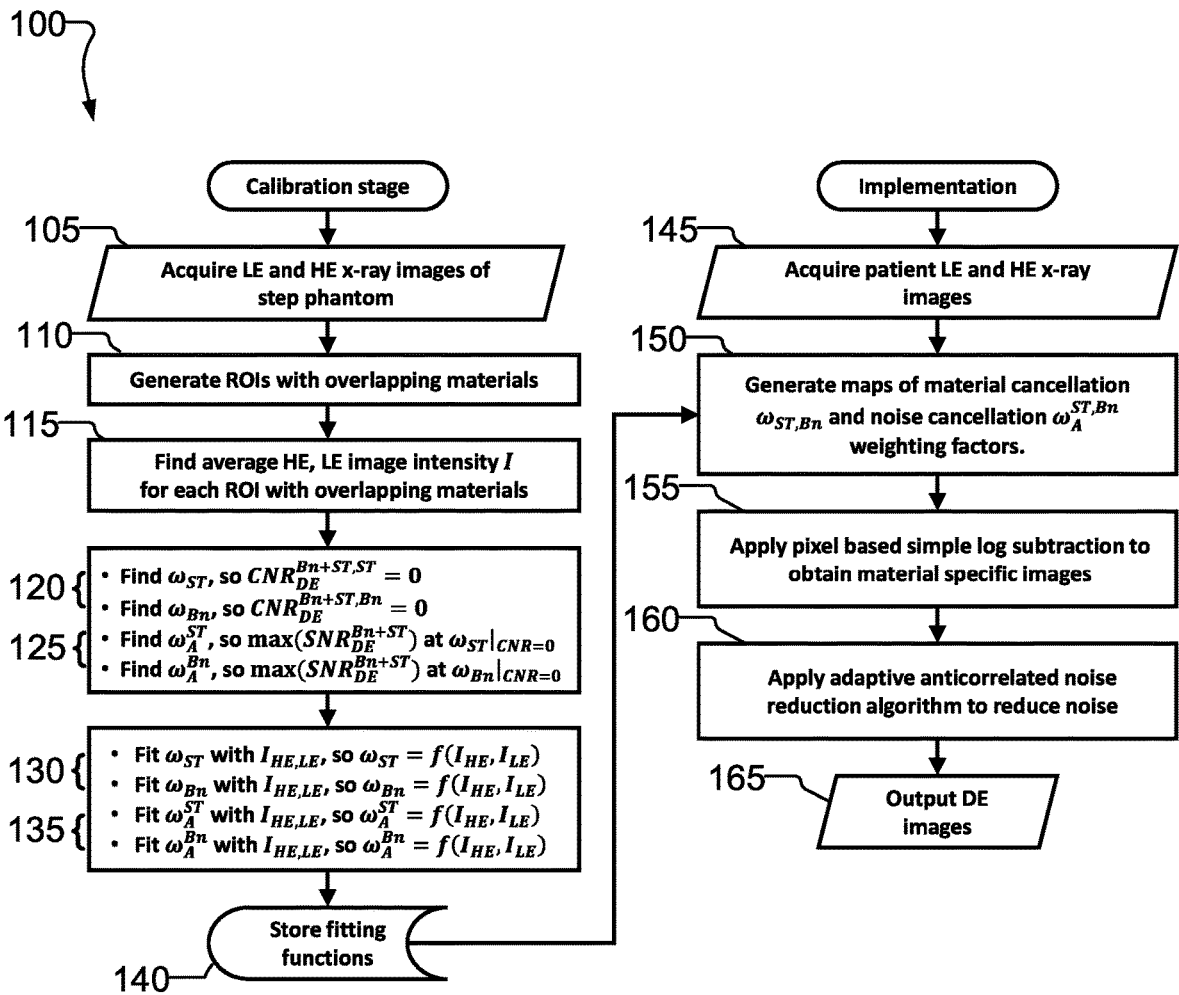
FIG. 1 is a block diagram showing an example method for using a step phantom to calibrate a fitting model for adaptive dual-energy imaging.

FIG. 1 shows a block diagram of an example method 100 for dual-energy imaging involving the use of a calibration step phantom. This example method 100 uses a step phantom for calibrating material cancellation $\omega_{ST,Bn}$ and noise reduction $\omega_A$ weighting factors (blocks 105-140). Method 100 implements the calibrated model on a patient image (blocks 145-165).

Block 105 comprises acquiring LE and HE x-ray images of a step phantom. The step phantom comprises overlapping slabs of soft tissue and bone mimicking materials. In some embodiments, a step phantom comprises overlapping layers of "solid water" for mimicking soft tissue (e.g. 0-30 cm with 5 cm step, Model 557-450 GAMMEX, Middleton, WI) and layers of bone mimicking material (e.g. 0-6 cm with 1 cm step, Model BN30-20-AB CIRS Inc, Norfolk, VA). Material thicknesses vary in the direction(s) orthogonal to the x-ray beam such that different combinations of material thicknesses can be simulated.

Method 100 proceeds to block 110 which comprises generating regions of interest which include overlapping materials. FIGS. 2A and 2B show example projection images of a calibration step phantom for an HE image and an LE image, respectively. The images of FIGS. 2A and 2B are example outputs from the performance of block 110. In this example embodiment, there are a total of 7×7 regions for each calibration image.

FIG. 2C shows an example step phantom which may be used for obtaining the projection images of FIGS. 2A and 2B. As illustrated, the FIG. 2C step phantom comprises six bone slabs and six solid water slabs of varying dimensions. As an illustrative example, image acquisition of the projection images may be performed using a clinical x-ray imaging system with HE beam parameters set to 140 kVp, 12 mAs, and LE beam parameters set to 60 kVp and 40 mAs. Image post-processing may include dark and flood field corrections.

It will be appreciated that phantoms of different sizes and with a different number of overlapping areas can be used in practising the invention. For example, the size of the step phantom may correspond to patients of different sizes, e.g. small, medium, and large patients. In some embodiments, calibrations based on images obtained from a plurality of differently sized step phantoms may be interpolated. This can advantageously increase the calibration accuracy and provide better material cancellation specific to the patient anatomy.

At block 115, a mean signal intensity is determined for the HE and LE x-ray images for each region of interest of overlapping materials. At block 120, method 100 comprises determining optimal material cancellation weighting factors $\omega_{ST,Bn}$ for bone and soft tissue. The material cancellation weighting factors $\omega_{ST}$ may be obtained by calculating the contrast-to-noise ratio (CNR) between regions of overlapping soft tissue and bone and corresponding soft tissue only regions. The $CNR_{DE}$ function for calculating an optimal weighting factor $\omega_{ST}$ for cancelling the bone signal can be expressed as:

$$CNR_{DE} = \frac{DE_{Bn,ST} - DE_{ST}}{\sqrt{\sigma_{Bn,ST}^2 + \sigma_{ST}^2}} \tag{3}$$

where $DE_{ST,Bn}$ is the DE signal in the region with overlapping materials, $DE_{ST}$ is the DE signal with soft tissue only, and $$\sigma_{Bn,ST}^2, \sigma_{ST}^2$$

is the corresponding noise in terms of the DE signals' variances. The DE signal value may be obtained using Equation (1) above. The weighting factor $\omega_{ST}$ which results in $CNR_{DE}$ of Equation (3) being set to zero can be determined to therefore ensure that the bone signal is cancelled. A similar procedure may be performed for obtaining the weighting factor $\omega_{Bn}$ for soft tissue cancellation, i.e. the optimal $\omega_{Bn}$ is obtained when CNR between regions of overlapping soft tissue and bone and corresponding bone only regions is set to zero.

Figure 3A:
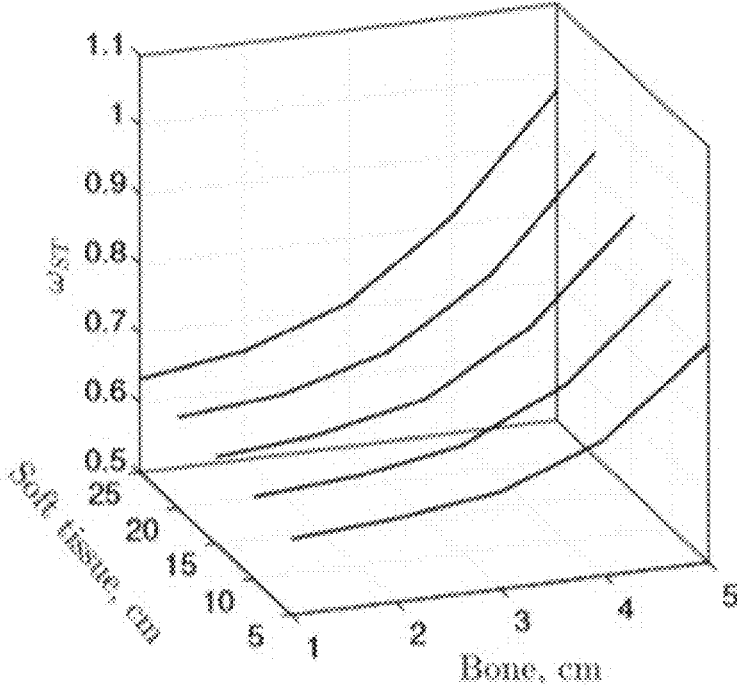
FIGS. 3A and 3B show graphs of soft tissue and bone material cancellation weighting factors for different material thicknesses, respectively.
Figure 3B:
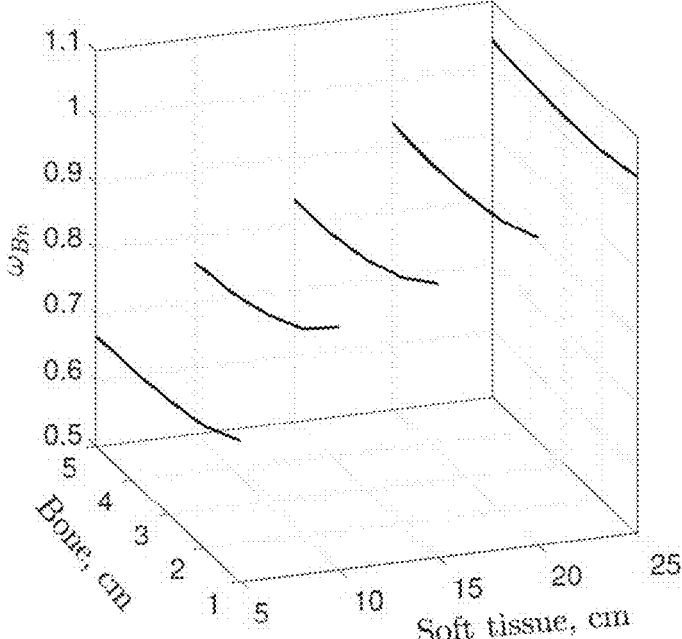

By performing block 120 on the x-ray images of the FIG. 2 example for each region of overlapping materials (total of 36 regions), bone and soft tissue cancellation weighting factors may be obtained. FIGS. 3A and 3B show example soft tissue and bone cancellation weighting factors $\omega_{ST}$ and $\omega_{Bn}$, respectively for differing material thicknesses according to the example step phantom configuration.

Method 100 then proceeds to block 125 which comprises determining weighting factors $\omega_A$ for noise cancellation.

11

According to an example embodiment, the ACNR noise reduction algorithm can be used for determining noise cancellation weighting factors $\omega_A$ for each material of interest. This may comprise maximizing the signal-to-noise (SNR) ratio of each region of the DE images with overlapping materials with material cancellation weighting factor w selected so that CNR=0 for a particular material. The SNR of the DE images, or $SNR_{DE}$, may for example have the form:

$$SNR_{DE} = \frac{DE_{Bn,ST}}{\sigma_{Bn,ST}} \qquad (4)$$

FIGS. 4A and 4B show example soft tissue and bone noise cancellation weighting factors $$\omega_A^{ST} \text{ and } \omega_A^{Bn},$$

respectively for differing material thicknesses according to the example step phantom configuration of FIG. 2.

At block 130, method 100 comprises fitting the material cancellation weighting factors $\omega_{ST}$ and $\omega_{Bn}$ (determined at block 120) as a function of the signal intensities of the x-ray projection images (determined at block 115). According to an example embodiment, the fitting process is performed using a standard (e.g. MathWorks, Natick, MA) fitting toolbox, by using "thinplateinterp" method. In other embodiments, lower and higher dimensional models may be used e.g. second-order polynomial, and $4^{th}$ and $5^{th}$ order polynomial models. However, such lower or higher dimensional models may result in images of lower quality due to overfitting or underfitting, and so a first order model is often appropriate.

Figures 5A, 5B:
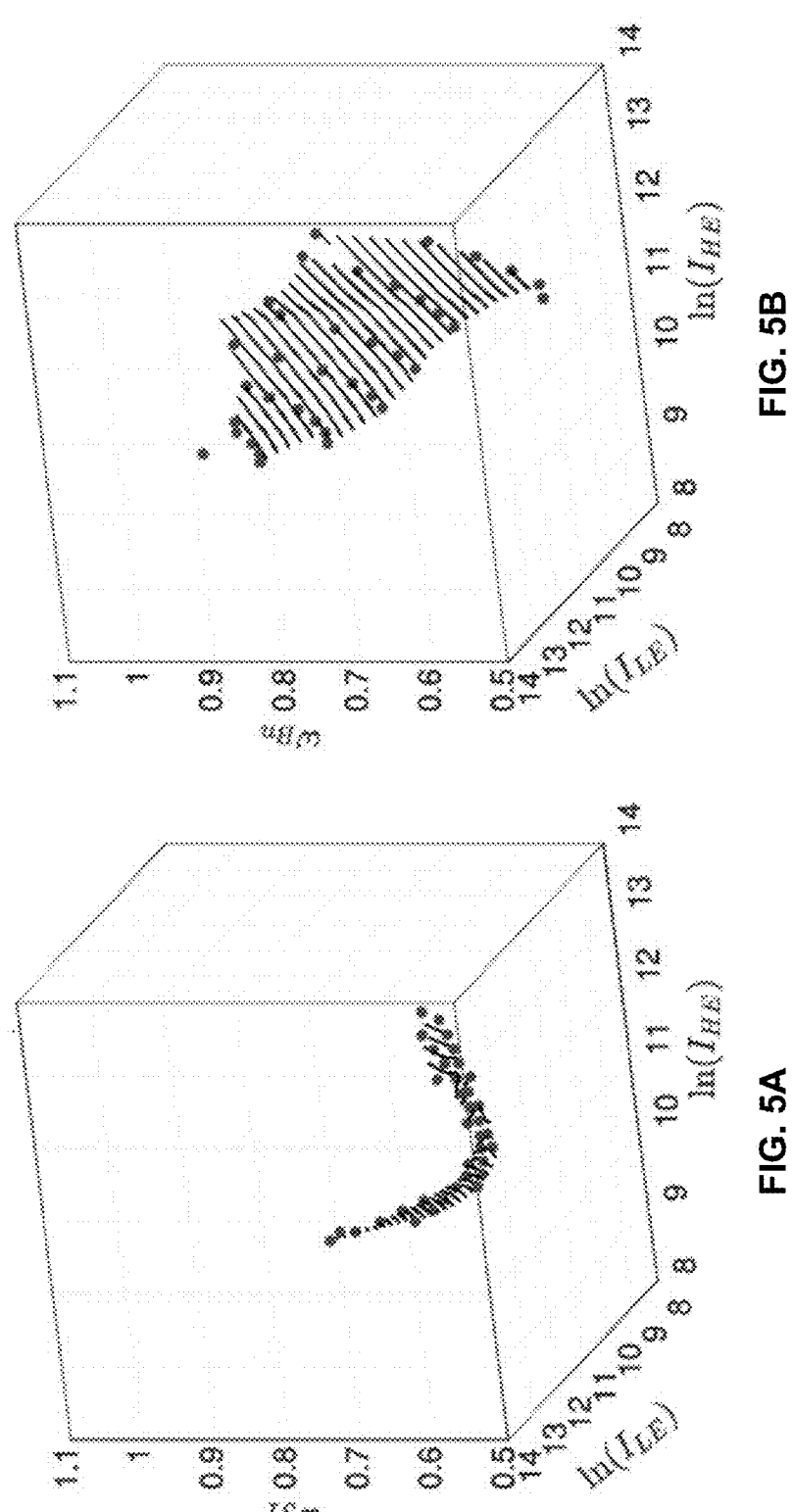
FIGS. 5A and 5B show fitted models for obtaining soft tissue and bone cancellation weighting factors, respectively.

FIGS. 5A and 5B show example fitted models for obtaining soft tissue and bone cancellation weighting factors $\omega_{ST}$ and $\omega_{Bn}$, respectively based on LE and HE signal intensities. The points are the measured optimal weighting factors from the step phantom (as shown in FIGS. 3A-D) while the lines are isolines of fitted surfaces.

Figures 6A, 6B:
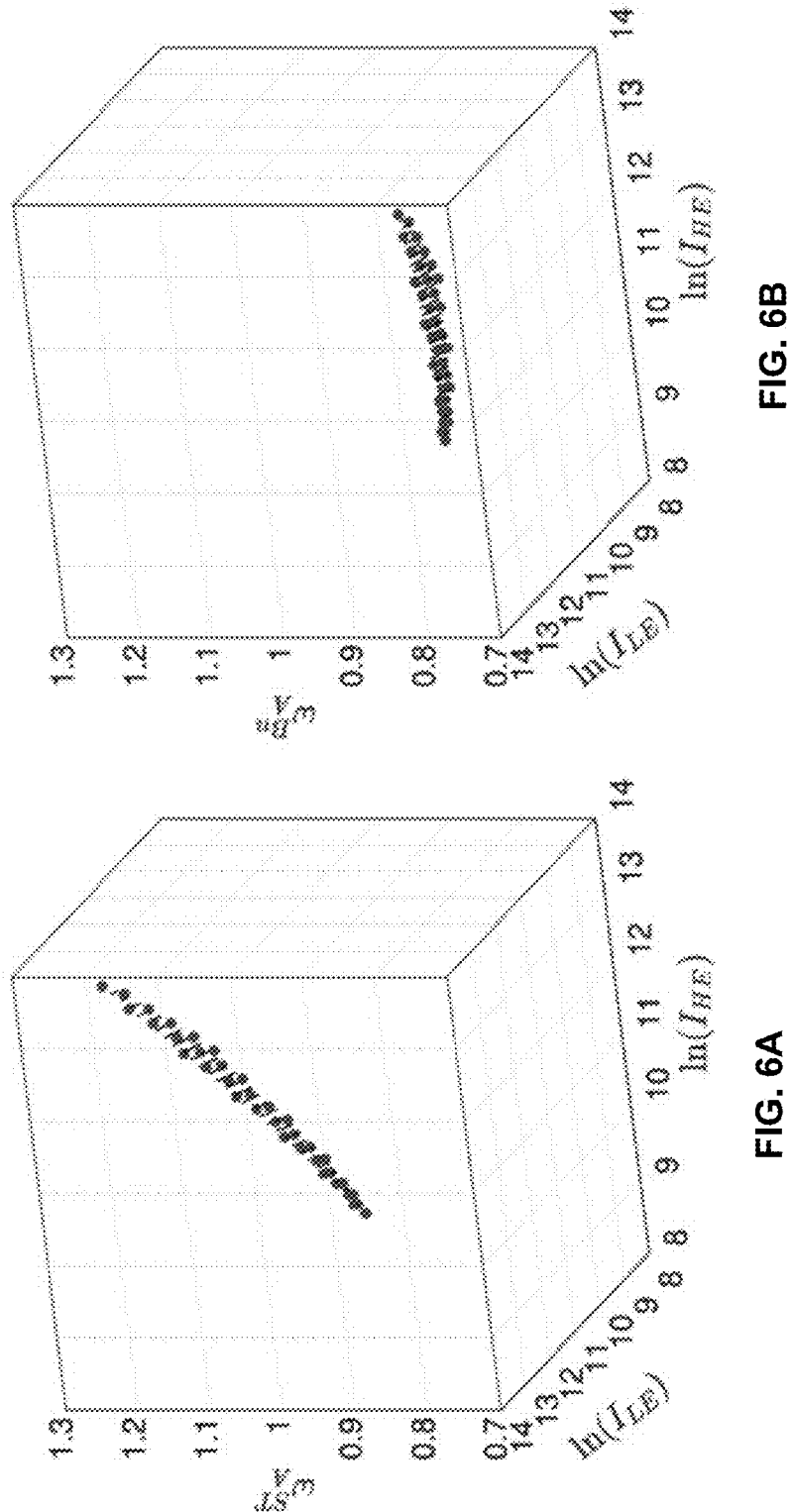
FIGS. 6A and 6B show fitted models for obtaining soft tissue and bone noise cancellation weighting factors, respectively.

Similarly, at block 135, the noise cancellation weighting factors $$\omega_A^{ST} \text{ and } \omega_A^{Bn}$$

are fit to a model as a function of the signal intensities of the x-ray projection images. The model fitting at block 135 may, for example, employ any of the same fitting methods described in relation to block 130. FIGS. 6A and 6B show example fitted models for obtaining soft tissue and bone noise cancellation weighting factors $$\omega_A^{ST} \text{ and } \omega_A^{Bn},$$

respectively based on LE and HE signal intensities.

Block 140 comprises storing the fitting functions obtained at blocks 130 and 135 to thus complete the "calibration" stage of method 100. Blocks 145-165 of method 100 represent the "implementation" stage, where the various stored fitting functions can be applied to specific patient images for obtaining material cancellation and noise cancellation weighting factors based on measured HE and LE pixel intensities. Using the described approach, no a priori CT image of the patient is required. Rather, information from the HE and LE images themselves can be used directly to calculate weighting factors. In some embodiments, an appropriate fitting function is pre-selected to allow for refined images to be obtained in real time.

Figure 7A:
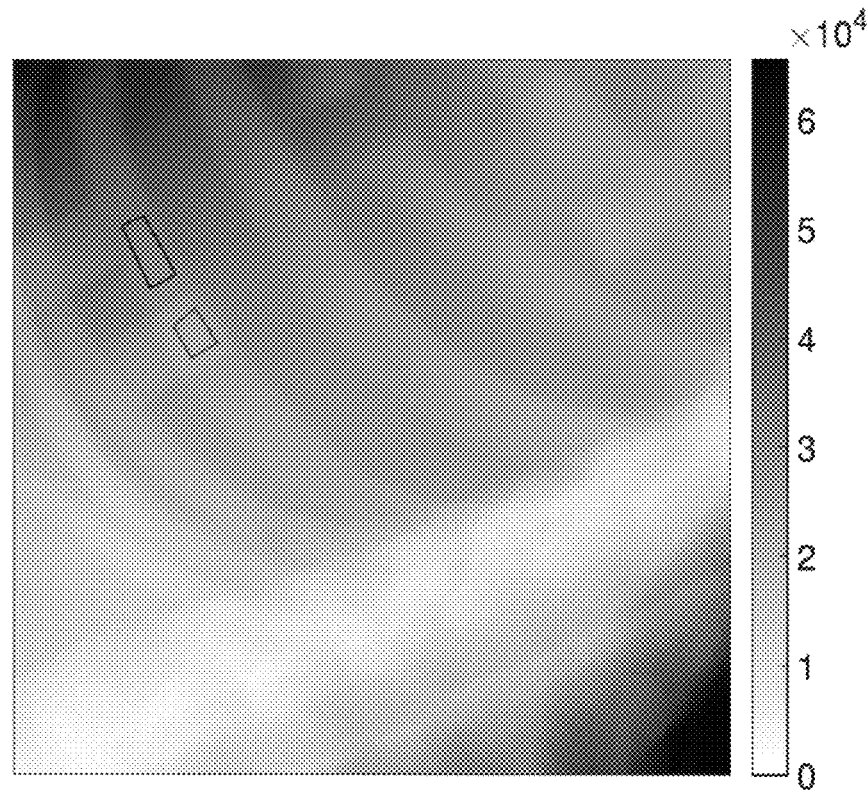
FIGS. 7A and 7B show example patient x-ray images.
Figure 7B:
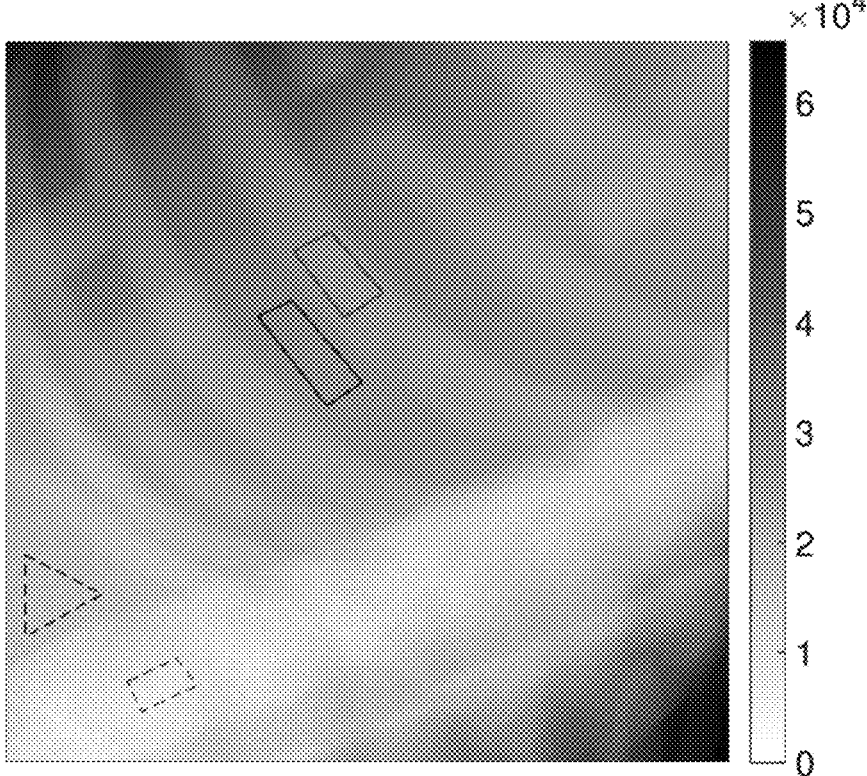

At block 145, patient LE and HE x-ray images are obtained. FIGS. 7A and 7B show example patient images obtained using an adult anthropomorphic Rando phantom (CIRS Inc, Norfolk, VA). In some embodiments, the image acquisition parameters are the same as those used for the step phantom at block 105.

FIGS. 7A and 7B show high energy and low energy images of the Rando phantom, respectively. In this illustrative example, a tumor was mimicked using a cylindrical solid water plug (14 mm diameter, 25 mm long), which is inserted in the lung tissue. FIGS. 7A and 7B do not show simple anterior-posterior or lateral views due to the geometry of the x-ray imaging system used, where beams incident on the patient at oblique angles (polar angle 42°, azimuthal angle 45°). The top-left and bottom-right in the images are anterior and posterior directions, respectively.

In the high energy image of FIG. 7A, the area enclosed by the upper rectangle is considered the tumor background while the area enclosed by the lower rectangle shows the tumor. In the low energy image of FIG. 7B, the area at the lower left corner enclosed by the dashed rectangle shows the spine while the area enclosed by the dashed triangle is considered its background. In the image of FIG. 7B, the area enclosed by the upper solid rectangle shows the rib and the area enclosed by the lower solid rectangle is considered its background. The noise and contrast of the obtained images may be evaluated with the CNR of the selected regions of interest (ROIs) (such as the areas indicated for the tumor, the spine, and the rib with the corresponding backgrounds in FIGS. 7A and 7B).

After completing block 145, method 100 proceeds to block 150 which comprises generating patient specific maps of material cancellation $\omega_{ST,Bn}$ and noise cancellation $$\omega_A^{ST,BN}$$

weighting factors according to the patient x-ray image. Specifically, block 150 uses the models fitted at blocks 130 and 135 to determine the material cancellation $\omega_{ST,Bn}$ and noise cancellation $$\omega_A^{ST,BN}$$

weighting factors based on the HE and LE pixel intensities of the patient image.

Figures 8A, 8B:
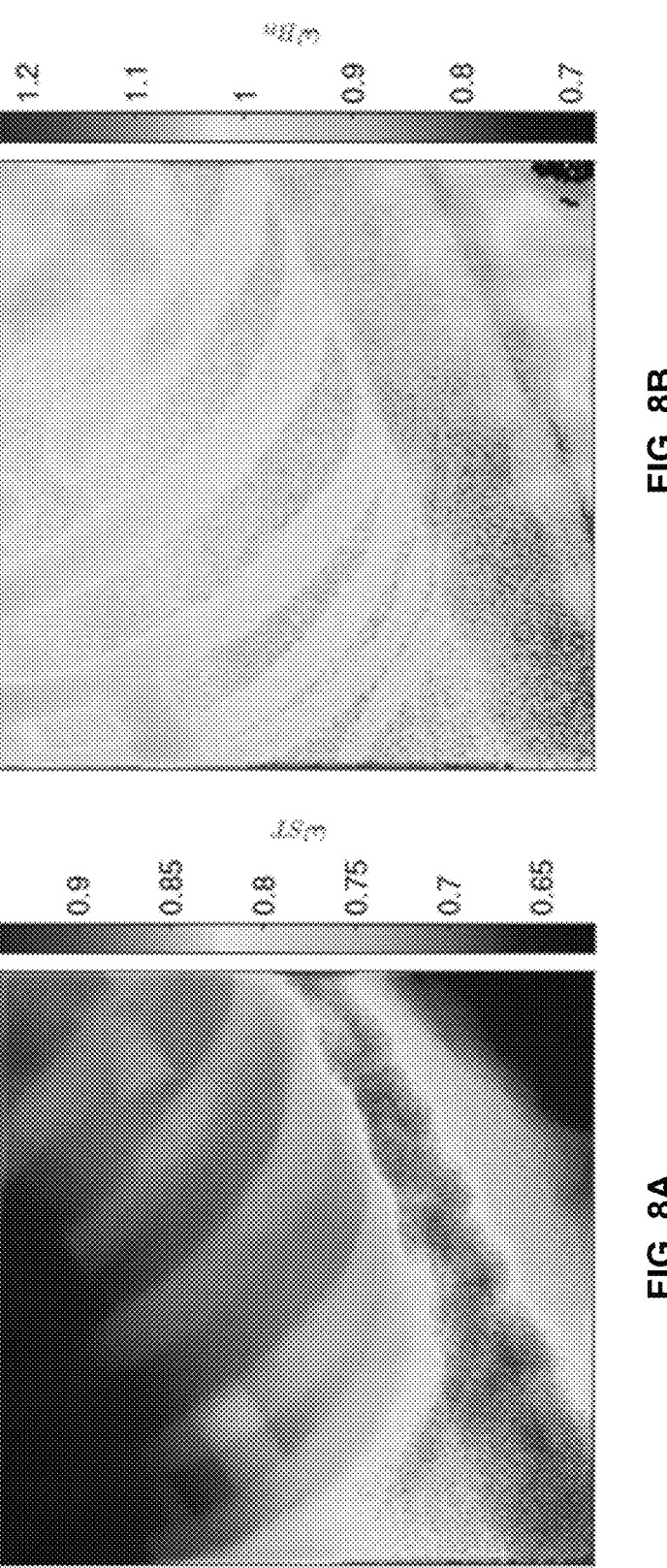
FIGS. 8A and 8B show maps of material cancellation weighting factors for soft tissue and bone, respectively.
Figures 9A, 9B:
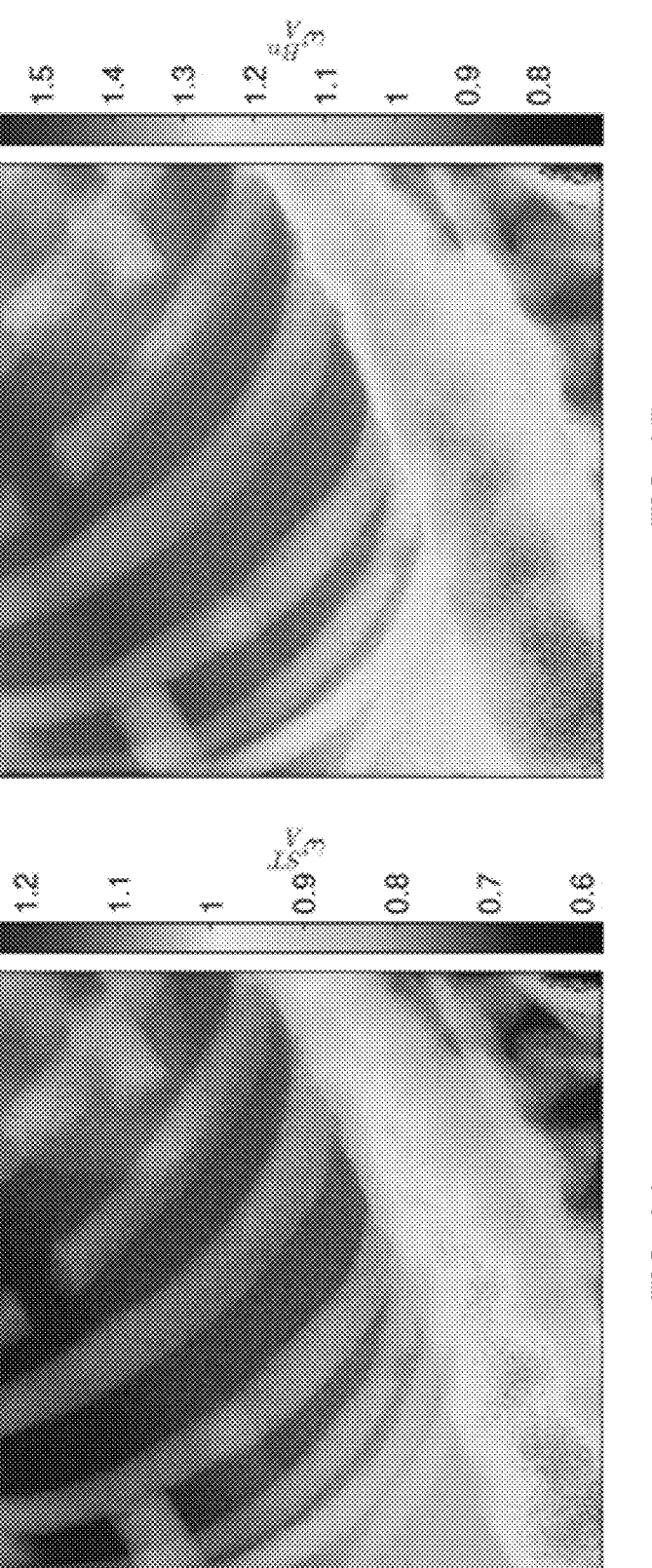
FIGS. 9A and 9B show maps of noise cancellation weighting factors for soft tissue and bone, respectively.

FIGS. 8A and 8B show resulting maps from the performance of block 150 for material cancellation weighting factors $$\omega_A^{ST} \text{ and } \omega_A^{Bn}$$

for soft tissue and bone, respectively. Similarly, FIGS. 9A and 9B show resulting maps for noise cancellation weighting factors

13

$$\omega_A^{ST} \text{ and } \omega_A^{Bn}$$

for soft tissue and bone, respectively.

At block 155, simple log subtraction (e.g. using Equation (1)) can be performed on the patient images on a pixel specific basis based on the maps obtained at block 150 to obtain material specific images (e.g. soft tissue specific or bone specific). This described method for obtaining material specific DE images on a spatially varying basis may be referred to as adaptive DE, or "aDE".

At block 160, ACNR (e.g. using Equation (2)) can be performed on the material specific images from block 155 based on the maps obtained at block 150 to obtain material specific noise reduction. This described method for spatially varied and material specific noise cancellation may be referred to as adaptive ACNR, or aACNR. The performance of block 160 outputs DE image 165.

To evaluate the performance of the proposed method, images obtained with four DE methods were obtained: a) SLS, b) adaptive DE (aDE) with no noise suppression, c) aDE and uniform ACNR, and d) aDE with adaptive ACNR (aACNR). Soft tissue only DE images generated in these four scenarios are shown in FIGS. 10A-10D. Similarly, bone only DE images generated in these four scenarios are shown in FIGS. 11A-11D.

Figure 10B:
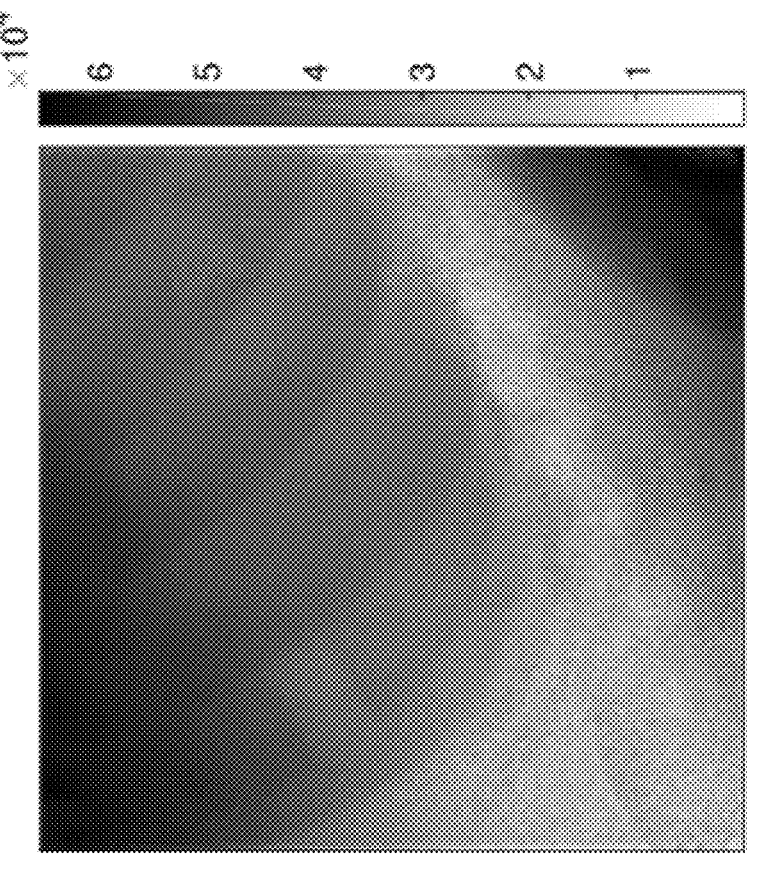
FIGS. 10A-10D show the results of different dual-energy imaging techniques in obtaining soft tissue only images.
Figure 10A:
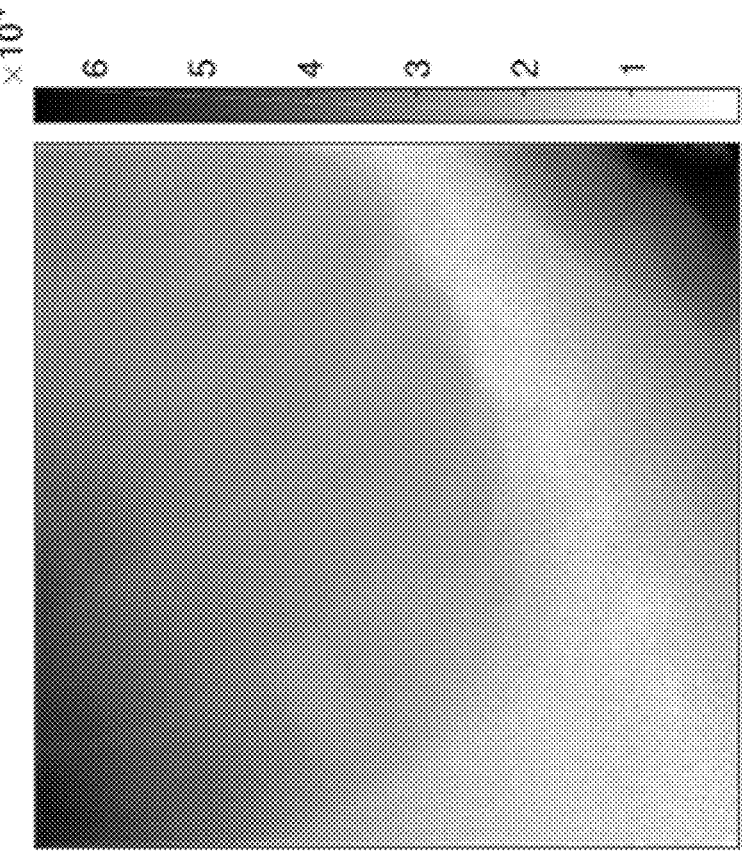
Figures 10C, 10D:
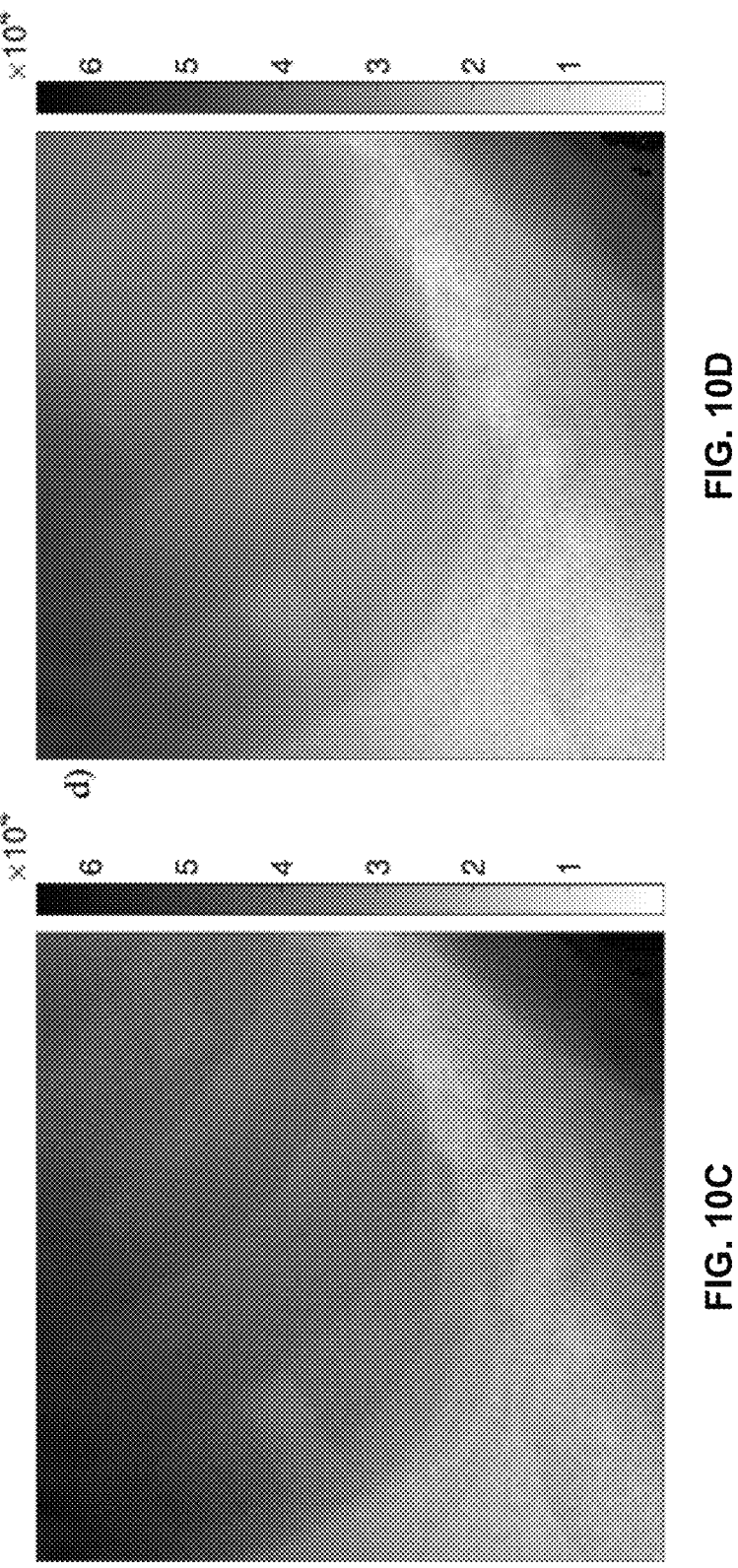
Figure 11B:
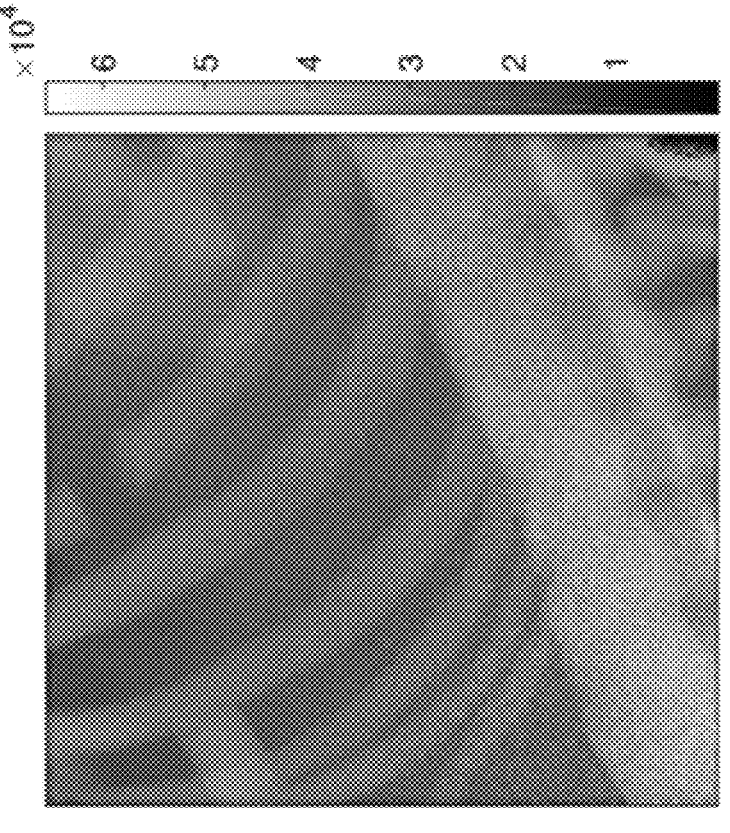
FIGS. 11A-11D show the results of different dual-energy imaging techniques in obtaining bone only images.
Figure 11A:
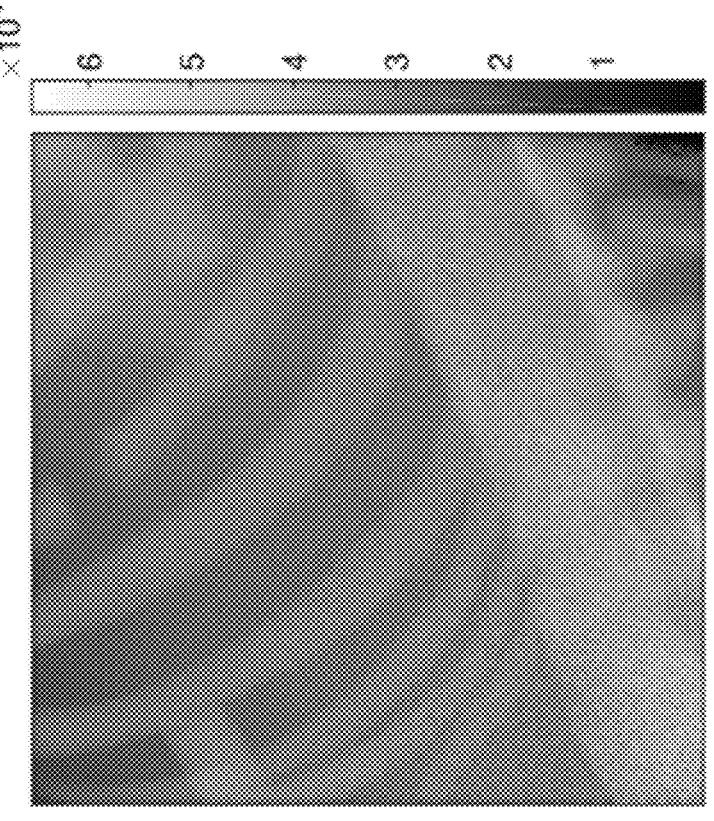
Figures 11C, 11D:
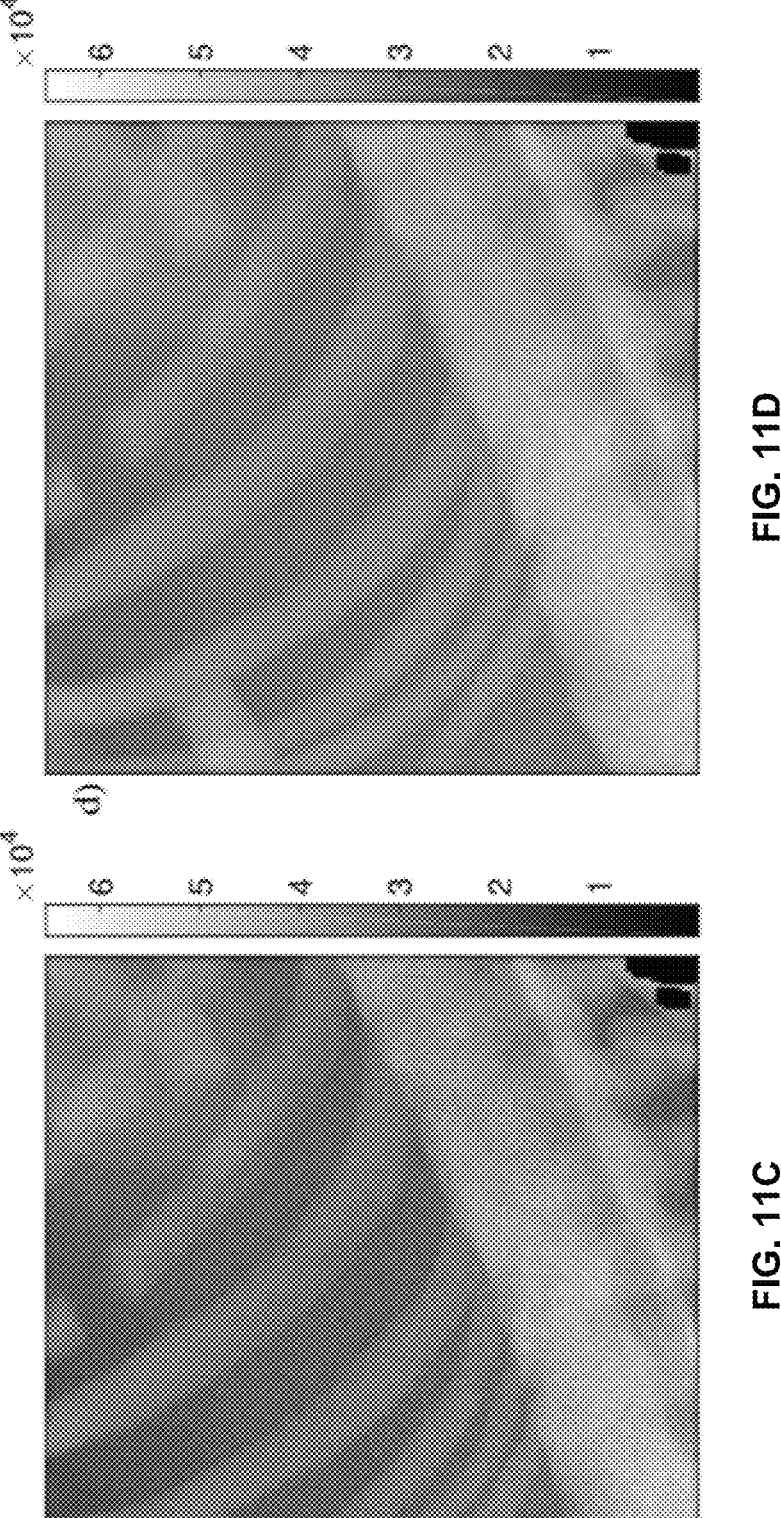

The images of FIGS. 10 and 11 show a qualitative improvement in DE image quality when the adaptive DE method is used for both tissue cancellation and noise suppression. For example, tumor contrast is increased in the x-ray image produced in FIG. 10D while the noise is reduced to a greater extent across the image compared to the other DE methods in FIGS. 10A-10C. Similarly, the x-ray image produced in FIG. 11D demonstrates improved bone contrast (of the rib and spine) with reduced noise across the image when the adaptive DE method is employed for both soft tissue cancellation and noise reduction.

To quantify these improvements in terms of CNR, the selected ROIs in FIG. 7 for the tumor and bones (i.e. rib and spine) were evaluated. The results are presented in Table 1, which indicates that the best CNR amongst the four evaluated DE methods is achieved when utilizing the adaptive DE with adaptive noise suppression.

TABLE 1

| CNR values of corresponding ROIs for four different DE methods | | | |
| --- | --- | --- | --- |
| | SLS | aDE | aDE & ACNR | aDE & aACNR |
| Tumor CNR | 4.15 | 4.43 | 4.13 | 4.56 |
| Rib CNR | 3.45 | 3.12 | 3.75 | 4.23 |
| Spine CNR | 2.40 | 2.99 | 5.07 | 5.78 |

Accordingly, the described adaptive DE method overcomes or reduces the limitations of conventional log-subtraction DE algorithms. The weighting factor in traditional SLS algorithms is uniform across the image and is typically selected for reducing the contrast between selected bone and soft-tissue regions. While such an approach may be appropriate in some scenarios, it does not ensure a complete unwanted material cancellation, especially for images with large variations of material thicknesses and densities. This is due to the polychromatic nature of clinical x-ray sources, which results in beam hardening effects.

Using non-constant (variable) weighting factors across the image allows all weighting factors to change when material thicknesses change. In the example results described above, while the weighting factor ranges appear to be small, they are applied logarithmically to obtain DE images, and thus, the impact can be significant. For example, values of the soft tissue cancellation weighting factor $\omega_{ST}$ increase when either soft tissue or bone thickness increased (see FIG. 3A). In other words, the pixel intensity decreases for either the LE or HE images (see FIG. 5A). In such cases, a greater contribution is required from the LE image to cancel a thicker bone, especially when the x-ray beam is harder.

In typical cases for all corresponding regions, $\omega_{Bn}$ is larger than $\omega_{ST}$, since $\mu^{HE}/\mu^{LE}$ of soft tissue is larger than that of bone. Values of $\omega_{Bn}$ also increase when the beam is hardened by increasing soft tissue thickness (see. FIG. 3B). However, the $\omega_{Bn}$ trend is opposite to that of $\omega_{ST}$ when bone thickness increases. The same trends can be observed in FIGS. 8A and 8B. Specifically, thicker regions require larger $\omega_{ST}$ and $\omega_{Bn}$, except bone regions reduce $\omega_{Bn}$ considerably, for example, in the areas of the ribs and spine.

Noise cancellation weighting factors show similar trends, as shown in FIGS. 4A and 4B. Noise cancellation weighting factor for bone $$\omega_A^{Bn}$$

is typically larger than $$\omega_A^{ST}$$

for corresponding regions. However, $$\omega_A^{ST} \text{ and } \omega_A^{Bn}$$

have different dependencies on material thickness.

$$\omega_A^{ST}$$

reaches a minimum at soft tissue thickness $$\omega_A^{ST}$$

and t=15 cm, whilst $$\omega_A^{Bn}$$

is maximized there. With the increase of the bone thickness, $$\omega_A^{ST}$$

is increasing and $$\omega_A^{Bn}$$

is decreasing. This agrees with the noise anti-correlation for material specific images.

As shown in the Rando phantom simulation of a patient anatomy, the fitted functions allow for accurate generation of material and noise cancellation weighting maps. Meanwhile, the calibration procedure does not require a large amount of imaging data. Visual inspection of the images showed the improvement of the image quality with the aDE method. This was supported by CNR evaluation. The addition of the aACNR method leads to a further increase of the image quality, as illustrated in Table 1.

The present methods for providing an adaptive DE method account for variations in beam attenuation across patient images (i.e. beam hardening effects), which leads to variations in material cancellation weighting factors as well as variations in noise levels. Furthermore, the described methods do not require a priori image data, and are computationally efficient. By fitting calibrated weighting factors with image intensities, a robust method for the generation of material and noise cancellation weighting maps is achieved. The described adaptive DE methods may be used in a number of applications, such as diagnostic imaging and IGRT applications for patient setup, tumor localization, and real-time tumor monitoring, for example.

The present invention may also be embodied in apparatuses configured to perform methods as described herein. The apparatuses may comprise data processors configured to receive pairs of image data corresponding to LE or HE images and to process the images as described herein to yield a digital output image. The output image may be stored in a data store, displayed on a display and/or printed. The apparatuses may comprise stored fitted models (fitting functions) for obtaining soft tissue and bone cancellation weighting factors $\omega_{ST}$ and $\omega_{Bn}$ respectively. The fitting functions may be in various forms such as lookup tables or software modules. The fitting functions may take as a key or input an intensity value and may produce as an output a corresponding weighting factor.

For example, data processors in various embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs"). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

The invention may also be provided in the form of a program product. The program product may comprise any non-transitory medium which carries a set of computer-readable instructions which, when executed by a data processor, cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

In addition or as an alternative to using a step phantom for calibration as described herein, one could use phantoms of other designs which present different thicknesses of materials that simulate different tissue types (e.g. bone and soft tissue) and/or DE images of one or more different people for which the thickness of different tissue types (e.g. bone and soft tissue) at different locations in the images are known.

Interpretation of Terms

Unless the context clearly requires otherwise, throughout the description and the claims:

"comprise", "comprising", and the like are to be construed in an inclusive sense, as opposed to an exclusive or exhaustive sense; that is to say, in the sense of "including, but not limited to";

"connected", "coupled", or any variant thereof, means any connection or coupling, either direct or indirect, between two or more elements; the coupling or connection between the elements can be physical, logical, or a combination thereof;

"herein", "above", "below", and words of similar import, when used to describe this specification, shall refer to this specification as a whole, and not to any particular portions of this specification;

"or", in reference to a list of two or more items, covers all of the following interpretations of the word: any of the items in the list, all of the items in the list, and any combination of the items in the list;

the singular forms "a", "an", and "the" also include the meaning of any appropriate plural forms.

Words that indicate directions such as "vertical", "transverse", "horizontal", "upward", "downward", "forward", "backward", "inward", "outward", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

For example:

while processes or blocks in example methods described herein are presented in a given order, alternative examples may perform processes or blocks in a different order that obtains the same or a similar result.

Other example methods may be obtained by deleting, moving, adding, subdividing, combining, and/or modifying processes or blocks in the described example methods to provide alternatives or subcombinations.

Individual processes or blocks may be implemented in a variety of different ways.

while certain processes or blocks are described as being performed in series, in some cases such processes or blocks may instead be performed in parallel, or may be performed at different times.

It is therefore intended that the following claims are interpreted to include all such variations as are within their intended scope.

Various features are described herein as being present in "some embodiments". Such features are not mandatory and may not be present in all embodiments. Embodiments of the invention may include zero, any one or any combination of two or more of such features. All possible combinations of such features are contemplated by this disclosure even where such features are shown in different drawings and/or described in different sections or paragraphs. This is limited only to the extent that certain ones of such features are incompatible with other ones of such features in the sense that it would be impossible for a person of ordinary skill in the art to construct a practical embodiment that combines such incompatible features. Consequently, the description that "some embodiments" possess feature A and "some embodiments" possess feature B should be interpreted as an express indication that the inventors also contemplate embodiments which combine features A and B (unless the description states otherwise or features A and B are fundamentally incompatible).

The invention has a number of non-limiting aspects. Non-limiting aspects of the invention comprise:

1. A method for processing x-ray images, the method comprising:

obtaining higher energy (HE) and lower energy (LE) x-ray images of a subject, determining intensity values of pairs of corresponding aligned pixels of the HE and LE images respectively, for each of the pairs of corresponding pixels, using the intensity values of the pair to determine first and second material cancellation weighting factors and a noise cancellation weighting factor, creating a first dual energy (DE) x-ray image by combining the HE and LE x-ray images by log subtraction of the intensity values of the pairs of corresponding aligned pixels of the HE and LE x-ray images using the first material cancellation weighting factor corresponding to the pair of corresponding aligned pixels to yield the logarithm of a corresponding pixel value for the first DE x-ray image;

creating a second dual energy (DE) x-ray image complementary to the first DE x-ray image by combining the HE and LE x-ray images by log subtraction of the intensity values of the pairs of corresponding aligned pixels of the HE and LE x-ray images using the second material cancellation weighting factor corresponding to the pair of corresponding aligned pixels to yield the logarithm of a corresponding pixel value for the second DE x-ray image; and processing pixels of the first DE x-ray image to reduce noise using the noise cancellation weighting factor corresponding to each of the pixels and the second DE x-ray image.

2. The method according to aspect 1 wherein processing the pixels of the first DE x-ray image to reduce noise comprises generating a noise cancellation image by convolving a logarithm of the second DE x-ray image with a high pass filter and for each of the pixels of the first DE x-ray image subtracting rom the logarithm of the corresponding pixel value of the first DE x-ray image a corresponding pixel value of the noise cancellation image weighted by the corresponding noise cancellation weighting factor.

3. The method according to aspect 1 wherein processing the pixels of the first DE x-ray image to reduce noise comprises, computing:

$$\ln(DE_{ACNR}) = \ln(DE) - \omega_A(\ln(DE_C) * h_{HPF})$$

where $DE_{ACNR}$ is an array of the pixel values of a noise-reduced version of the first DE x-ray image, DE is an array of the pixel values of the first DE x-ray image, $\omega_A$ is the corresponding noise cancellation weighting factor, $DE_C$ is an array of the pixel values of the second DE x-ray image and $*h_{HPF}$ denotes a convolution with a high-pass filter.

4. The method according to any of aspects 1 to 3 wherein one of the first and second material cancellation weighting factors is a bone cancellation weighting factor and the other one of the first and second material cancellation weighting factors is a soft tissue cancellation weighting factor.

5. The method according to any of aspects 1 to 4 wherein the method comprises applying dark field and flood field corrections to one or both of the HE and LE x-ray images.

6. The method according to any of aspects 1 to 5 wherein using the intensity values of the pair to determine the first and second material cancellation weighting factors comprises inputting the intensity values of the pair into first and second fitted models which relate pairs of corresponding intensity values of the LE and HE x-ray images to the first and second material cancellation weighting factors respectively.

7. The method according to aspect 6 wherein the first and second fitted models comprise first and second calibration functions that each take as arguments a pair of an intensity value from the LE x-ray image and a corresponding intensity value from the HE x-ray image and the method comprises receiving the first and second material cancellation weighting factors as outputs of the first and second calibration functions respectively.

8. The method according to aspect 6 wherein the first and second fitted models are respectively embodied in first and second lookup tables wherein using the intensity values of the pair to determine the first and second material cancellation weighting factors comprises using the intensity values of the pair as keys for the first and second lookup tables and receiving the first and second material cancellation weighting factors as outputs of the first and second lookup tables respectively.

9. The method according to any of aspects 6 to 8 wherein the first and second fitted models are obtained by:

obtaining HE and LE x-ray images of a phantom comprising a plurality of different regions, each of the regions of the phantom comprising a first material, a second material or overlapping first and second overlapping materials;

identifying the regions of the phantom in the HE and LE x-ray images of the phantom;

determining an average intensity for each of the identified regions in each of the HE and LE x-ray images of the phantom;

determining a model material cancellation weighting factor for each of the first material and the second material for each of the regions of the phantom; and fitting the model material cancellation weighting factor for the first material for the regions of the phantom as a function of the average intensities of the HE and LE x-ray images of the phantom for the regions of the phantom to provide the first fitted model; and fitting the model material cancellation weighting factor for the second material for the regions of the phantom as a function of the average intensities of the HE and LE x-ray images of the phantom for the regions of the phantom to provide the second fitted model.

10. The method according to aspect 9 wherein one of the first and second materials is a bone mimicking material and the other one of the first and second materials is a soft tissue mimicking material.

11. The method according to aspect 9 or 10 wherein determining the model material cancellation weighting factor for each of the first and second materials is based on achieving a contrast to noise ratio (CNR) of zero between regions in which the first and second materials overlap and regions comprising only the first or second material respectively.

12. The method according to any of aspects 9 to 11 wherein the phantom is a step phantom comprising slabs of soft tissue mimicking material and bone mimicking material wherein each of the regions has a corresponding thickness of the soft tissue mimicking material or a corresponding thickness of the bone mimicking material or a corresponding thickness of the soft tissue mimicking material or a corresponding thickness of the bone mimicking material.

13. The method according to any of aspects 1 to 12 wherein using the intensity values of the pair to determine the noise cancellation weighting factor comprises inputting the intensity values of the pair into a first fitted noise cancellation model which relates pairs of corresponding intensity values of the LE and HE x-ray images to the noise cancellation weighting factor.

14 The method according to aspect 13 wherein the first fitted noise cancellation model comprises a first noise cancellation function that takes as arguments a pair of an intensity value from the LE x-ray image and a corresponding intensity value from the HE x-ray image and the method comprises receiving the noise cancellation weighting factor as an output of the first noise cancellation calibration function.

15. The method according to aspect 13 wherein the first fitted noise cancellation model is embodied in a first noise cancellation lookup table and wherein using the intensity values of the pair to determine the noise cancellation weighting factor comprises using the intensity values of the pair as keys for the first noise cancellation lookup table and receiving the noise cancellation weighting factor as an outputs of the first noise cancellation lookup table.

16. The method according to any of aspects 13 to 15 wherein the first fitted noise cancellation model is obtained by:

obtaining HE and LE x-ray images of a phantom comprising a plurality of different regions, each of the regions of the phantom comprising a first material, a second material or both the first and second materials overlapping;

identifying the regions of the phantom in the HE and LE x-ray images of the phantom;

determining an average intensity for each of the identified regions in each of the HE and LE x-ray images of the phantom;

determining a first model noise cancellation weighting factor corresponding to the first material for each of the regions of the phantom by the ACNR method; and fitting the first model material cancellation weighting factors for the first material for the regions of the phantom as a function of the average intensities of the HE and LE x-ray images of the phantom for the regions of the phantom to provide the first fitted noise cancellation model.

17. The method according to aspect 16 further comprising providing a second fitted noise cancellation model, the second fitted noise cancellation model being generated by: determining a second model noise cancellation weighting factor corresponding to the second material for each of the regions of the phantom by the ACNR method; and fitting the second model noise cancellation weighting factors for the second material for the regions of the phantom as a function of the average intensities of the HE and LE x-ray images of the phantom for the regions of the phantom to provide the second fitted noise cancellation model.

18. The method according to any of aspects 16 to 17 wherein determining the first model noise cancellation weighting factors comprises generating a first dual energy (DE) x-ray image of the phantom by combining the HE and LE x-ray images of the phantom by log subtraction of the intensity values of the pairs of corresponding aligned pixels of the HE and LE x-ray images using the first material cancellation weighting factor corresponding to the pair of corresponding aligned pixels to yield the logarithm of a corresponding pixel value for the first DE x-ray image of the phantom and selecting values for the first model noise cancellation weighting factors to maximize the signal-tonoise (SNR) ratio for each region of the phantom in the first DE x-ray image of the phantom.

19. The method according to any of aspects 16 to 18 wherein the phantom is a step phantom comprising slabs of soft tissue mimicking material and bone mimicking material wherein each of the regions has a corresponding thickness of the soft tissue mimicking material or a corresponding thickness of the bone mimicking material or a corresponding thickness of the soft tissue mimicking material or a corresponding thickness of the bone mimicking material.

20. The method according to any of aspects 1 to 19 wherein acquiring the HE x-ray image comprises using a beam energy of about 140 kVp, 21. The method according to any of aspects 1 to 20 wherein acquiring the LE x-ray image comprises using a beam energy of about 60 kVp.

22. A method for dual energy x-ray imaging comprising:
   obtaining higher energy (HE) and lower energy (LE) x-ray images of a subject,
   based on pixel intensities of the HE and LE x-ray images, generating patient specific maps of material cancellation $\omega_{ST,Bn}$ and noise cancellation $$\omega_A^{ST,Bn}$$

weighting factors and combining the LE and HE x-ray images to yield a dual-energy (DE) x-ray image using the material cancellation $\omega_{ST,Bn}$ and noise cancellation $$\omega_A^{ST,Bn}$$

weighting factors.

23. The method according to aspect 22 wherein combining the LE and HE x-ray images comprises log subtraction.

24. The method according to aspect 23 wherein the log subtraction comprises:

$$\ln(DE)=\ln(HE)-\omega_{ST,Bn}\ln(LE)$$

where DE is an array of the pixel values of the DE x-ray image, HE is an array of the pixel values of the HE x-ray image, LE is an array of the pixel values of the LE x-ray image and, $\omega_{ST,BnA}$ is the corresponding material cancellation weighting factor, ST indicates soft tissue, Bn indicates bone.

25. A method for adaptive dual-energy imaging, the method comprising:
   calibrating first and second fitted models respectively for first and second material cancellation weighting factors, wherein calibrating the first and second fitted models comprises:
      acquiring higher energy (HE) and lower energy (LE) x-ray images of a step phantom comprising a first material and a second material;
      finding regions of interest in the HE and LE x-ray images wherein the regions of interest correspond portions of the step phantom in which the first and second materials overlap;
      determining an average intensity for each region of interest in each of the HE and LE x-ray images;

determining a model material cancellation weighting factor for each of the first material and a second material for each of the regions of interest; and
fitting the model material cancellation weighting factors for the first and second materials respectively as a function of the signal intensities of the HE and LE x-ray images to provide the first and second fitted models.

26. The method according to aspect 25 comprising:
   determining a model noise cancellation weighting factor for each of the first and second materials for each of the regions of interest; and
   fitting the model noise cancellation weighting factors for the first and second materials respectively to first and second noise cancellation fitted models.

27. The method according to aspect 25 or 26 comprising:
   acquiring HE and LE x-ray images of a subject;
   generating a material cancellation map of subject-specific location-specific material cancellation weighting factors for the subject by for each of a plurality of locations using corresponding intensity values of the HE and LE x-ray images of the subject to obtain a corresponding material cancellation weighting factor from one of the first and second fitted models; and
   applying the material cancellation map to combine the HE and LE images of the subject into a DE image of the subject.

28. The method according to aspect 26 comprising:
   acquiring HE and LE x-ray images of a subject;
   generating a material cancellation map of subject-specific location-specific material cancellation weighting factors for the subject by for each of a plurality of locations using corresponding intensity values of the HE and LE x-ray images of the subject to obtain a corresponding material cancellation weighting factor from one of the first and second fitted models;
   applying the material cancellation map to combine the HE and LE x-ray images of the subject into a DE x-ray image of the subject;
   generating a noise cancellation map of subject-specific noise cancellation weighting factors from one of the first and second noise cancellation fitted models for each of a plurality of locations in the DE x-ray image of the subject; and
   applying the noise cancellation map to the DE x-ray image of the subject.

29. The method according to any of aspects 26 to 28 wherein determining the model noise cancellation weighting factors for the first and second materials is based on maximizing a signal to noise ratio (SNR).

30. The method according to aspect 28 wherein applying the material cancellation map comprises performing log subtraction of the HE and LE images of the subject to produce the DE x-ray image of the subject and wherein applying the noise cancellation map comprises performing ACNR on the DE x-ray image of the subject.

31. The method according to aspect 25 wherein determining the model material cancellation weighting factor for each of the first and second materials is based on achieving a CNR of zero between regions of overlapping first and second materials and regions comprising only first and second materials, respectively.

32. Apparatus for dual energy (DE) x-ray imaging comprising a data processor configured by computer executable instructions to perform a method according to any one of aspects 1 to 31.

33. Apparatus for dual energy (DE) x-ray imaging comprising:

first and second fitted material cancellation models respectively corresponding to first and second materials, each of the first and second fitted material cancellation models comprising an input for receiving an intensity value for a pixel of a higher energy (HE) x-ray image and an input for receiving an intensity value for a pixel of a lower energy (LE) x-ray image and configured to output a material cancellation weighting factor corresponding to intensity values presented at the inputs; and a data processor configured to:

process higher energy (HE) and lower energy (LE) x-ray images of a subject to obtain intensity values of pairs of corresponding aligned pixels of the HE and LE images respectively, for each of the pairs of corresponding pixels, using the intensity values of the pair as inputs to each of the first and second fitted material cancellation models to obtain corresponding first and second material cancellation weighting factors; and creating a first dual energy (DE) x-ray image by combining the HE and LE x-ray images by log subtraction of the intensity values of the pairs of corresponding aligned pixels of the HE and LE x-ray images using the first material cancellation weighting factor corresponding to the pair of corresponding aligned pixels to yield the logarithm of a corresponding pixel value for the first DE x-ray image; and creating a second dual energy (DE) x-ray image complementary to the first DE x-ray image by combining the HE and LE x-ray images by log subtraction of the intensity values of the pairs of corresponding aligned pixels of the HE and LE x-ray images using the second material cancellation weighting factor corresponding to the pair of corresponding aligned pixels to yield the logarithm of a corresponding pixel value for the second DE x-ray image.

34. The apparatus according to aspect 33 further comprising:

first and second fitted noise cancellation models respectively corresponding to the first and second materials, each of the first and second fitted noise cancellation models comprising an input for receiving an intensity value for a pixel of the higher energy (HE) x-ray image and an input for receiving an intensity value for a pixel of the lower energy (LE) x-ray image and configured to output a noise cancellation weighting factor corresponding to intensity values presented at the inputs;

wherein the processor is further configured to:

for each of the pairs of corresponding pixels, using the intensity values of the pair as inputs to one of the first and second fitted noise cancellation models to obtain a corresponding noise cancellation weighting factor; and processing pixels of the first DE x-ray image to reduce noise using the corresponding noise cancellation weighting factors.

35. A computer program product comprising a tangible medium storing machine readable, machine executable instructions that, when executed by a data processor cause the data processor to execute a method according to any one of aspects 1 to 31.

36. Apparatus comprising new and inventive feature, combination of features or subcombination of features as described herein.

37. Methods comprising any new and inventive step, act, combination of steps and/or acts or subcombination of steps and/or acts as described herein.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

The invention claimed is:

1. A method for processing x-ray images, the method comprising:

obtaining higher energy (HE) and lower energy (LE) x-ray images of a subject, determining intensity values of pairs of corresponding aligned pixels of the HE and LE images respectively, for each of the pairs of corresponding pixels, using the intensity values of the pair to determine first and second material cancellation weighting factors and a noise cancellation weighting factor, creating a first dual energy (DE) x-ray image by combining the HE and LE x-ray images by log subtraction of the intensity values of the pairs of corresponding aligned pixels of the HE and LE x-ray images using the first material cancellation weighting factor corresponding to the pair of corresponding aligned pixels to yield the logarithm of a corresponding pixel value for the first DE x-ray image;

creating a second dual energy (DE) x-ray image complementary to the first DE x-ray image by combining the HE and LE x-ray images by log subtraction of the intensity values of the pairs of corresponding aligned pixels of the HE and LE x-ray images using the second material cancellation weighting factor corresponding to the pair of corresponding aligned pixels to yield the logarithm of a corresponding pixel value for the second DE x-ray image; and processing pixels of the first DE x-ray image to reduce noise using the noise cancellation weighting factor corresponding to each of the pixels and the second DE x-ray image.

2. The method according to claim 1 wherein processing the pixels of the first DE x-ray image to reduce noise comprises generating a noise cancellation image by convolving a logarithm of the second DE x-ray image with a high pass filter and for each of the pixels of the first DE x-ray image subtracting from the logarithm of the corresponding pixel value of the first DE x-ray image a corresponding pixel value of the noise cancellation image weighted by the corresponding noise cancellation weighting factor.

3. The method according to claim 1 wherein processing the pixels of the first DE x-ray image to reduce noise comprises, computing:

$$\ln(DE_{ACNR}) = \ln(DE) - \omega_A(\ln(DE_C) * h_{HPF})$$

where $DE_{ACNR}$ is an array of the pixel values of a noise-reduced version of the first DE x-ray image, DE is an array of the pixel values of the first DE x-ray image, $\omega_A$ is the corresponding noise cancellation weighting factor, $DE_C$ is an array of the pixel values of the second DE x-ray image and $*h_{HPF}$ denotes a convolution with a high-pass filter.

4. The method according to claim 1 wherein one of the first and second material cancellation weighting factors is a bone cancellation weighting factor and the other one of the first and second material cancellation weighting factors is a soft tissue cancellation weighting factor.

5. The method according to claim 1 wherein using the intensity values of the pair to determine the first and second material cancellation weighting factors comprises inputting the intensity values of the pair into first and second fitted models which relate pairs of corresponding intensity values of the LE and HE x-ray images to the first and second material cancellation weighting factors respectively.

6. The method according to claim 5 wherein the first and second fitted models comprise first and second calibration functions that each take as arguments a pair of an intensity value from the LE x-ray image and a corresponding intensity value from the HE x-ray image and the method comprises receiving the first and second material cancellation weighting factors as outputs of the first and second calibration functions respectively.

7. The method according to claim 5 wherein the first and second fitted models are respectively embodied in first and second lookup tables wherein using the intensity values of the pair to determine the first and second material cancellation weighting factors comprises using the intensity values of the pair as keys for the first and second lookup tables and receiving the first and second material cancellation weighting factors as outputs of the first and second lookup tables respectively.

8. The method according to claim 5 wherein the first and second fitted models are obtained by:

obtaining HE and LE x-ray images of a phantom comprising a plurality of different regions, each of the regions of the phantom comprising a first material, a second material or overlapping first and second overlapping materials;

identifying the regions of the phantom in the HE and LE x-ray images of the phantom;

determining an average intensity for each of the identified regions in each of the HE and LE x-ray images of the phantom;

determining a model material cancellation weighting factor for each of the first material and the second material for each of the regions of the phantom; and fitting the model material cancellation weighting factor for the first material for the regions of the phantom as a function of the average intensities of the HE and LE x-ray images of the phantom for the regions of the phantom to provide the first fitted model; and fitting the model material cancellation weighting factor for the second material for the regions of the phantom as a function of the average intensities of the HE and LE x-ray images of the phantom for the regions of the phantom to provide the second fitted model.

9. The method according to claim 8 wherein one of the first and second materials is a bone mimicking material and the other one of the first and second materials is a soft tissue mimicking material.

10. The method according to claim 8 wherein determining the model material cancellation weighting factor for each of the first and second materials is based on achieving a contrast to noise ratio (CNR) of zero between regions in which the first and second materials overlap and regions comprising only the first or second material respectively.

11. The method according to claim 8 wherein the phantom is a step phantom comprising slabs of soft tissue mimicking material and bone mimicking material wherein each of the regions has a corresponding thickness of the soft tissue mimicking material or a corresponding thickness of the bone mimicking material or a corresponding thickness of the soft tissue mimicking material or a corresponding thickness of the bone mimicking material.

12. The method according to claim 1 wherein using the intensity values of the pair to determine the noise cancellation weighting factor comprises inputting the intensity values of the pair into a first fitted noise cancellation model which relates pairs of corresponding intensity values of the LE and HE x-ray images to the noise cancellation weighting factor.

13. The method according to claim 12 wherein the first fitted noise cancellation model comprises a first noise cancellation calibration function that takes as arguments a pair of an intensity value from the LE x-ray image and a corresponding intensity value from the HE x-ray image and the method comprises receiving the noise cancellation weighting factor as an output of the first noise cancellation calibration function.

14. The method according to claim 12 wherein the first fitted noise cancellation model is embodied in a first noise cancellation lookup table and wherein using the intensity values of the pair to determine the noise cancellation weighting factor comprises using the intensity values of the pair as keys for the first noise cancellation lookup table and receiving the noise cancellation weighting factor as outputs of the first noise cancellation lookup table.

15. The method according to claim 12 wherein the first fitted noise cancellation model is obtained by:

obtaining HE and LE x-ray images of a phantom comprising a plurality of different regions, each of the regions of the phantom comprising a first material, a second material or both the first and second materials overlapping;

identifying the regions of the phantom in the HE and LE x-ray images of the phantom;

determining an average intensity for each of the identified regions in each of the HE and LE x-ray images of the phantom;

determining a first model noise cancellation weighting factor corresponding to the first material for each of the regions of the phantom by an anti-correlated noise reduction (ACNR) method; and fitting the first model material cancellation weighting factors for the first material for the regions of the phantom as a function of the average intensities of the HE and LE x-ray images of the phantom for the regions of the phantom to provide the first fitted noise cancellation model.

16. The method according to claim 15 further comprising providing a second fitted noise cancellation model, the second fitted noise cancellation model being generated by:

determining a second model noise cancellation weighting factor corresponding to the second material for each of the regions of the phantom by the ACNR method; and fitting the second model noise cancellation weighting factors for the second material for the regions of the phantom as a function of the average intensities of the HE and LE x-ray images of the phantom for the regions of the phantom to provide the second fitted noise cancellation model.

17. The method according to claim 15 wherein determining the first model noise cancellation weighting factors comprises generating a first dual energy (DE) x-ray image of the phantom by combining the HE and LE x-ray images of the phantom by log subtraction of the intensity values of the pairs of corresponding aligned pixels of the HE and LE x-ray images using the first material cancellation weighting factor corresponding to the pair of corresponding aligned pixels to yield the logarithm of a corresponding pixel value for the first DE x-ray image of the phantom and selecting values for the first model noise cancellation weighting factors to maximize the signal-to-noise (SNR) ratio for each region of the phantom in the first DE x-ray image of the phantom.

18. The method according to claim 15 wherein the phantom is a step phantom comprising slabs of soft tissue mimicking material and bone mimicking material wherein each of the regions has a corresponding thickness of the soft tissue mimicking material or a corresponding thickness of the bone mimicking material or a corresponding thickness of the soft tissue mimicking material or a corresponding thickness of the bone mimicking material.

19. A method for dual energy x-ray imaging comprising:
obtaining higher energy (HE) and lower energy (LE) x-ray images of a subject,
based on pixel intensities of the HE and LE x-ray images, generating patient specific maps of material cancellation $\omega_{ST,Bn}$ and noise cancellation $\omega_A^{ST,Bn}$ weighting factors and combining the LE and HE x-ray images to yield a dual-energy (DE) x-ray image using the material cancellation $\omega_{ST,Bn}$ and noise cancellation $\omega_A^{ST,Bn}$ weighting factors.

20. Apparatus for dual energy (DE) x-ray imaging comprising:
first and second fitted material cancellation models respectively corresponding to first and second materials, each of the first and second fitted material cancellation models comprising an input for receiving an intensity value for a pixel of a higher energy (HE) x-ray image and an input for receiving an intensity value for a pixel of a lower energy (LE) x-ray image and configured to output a material cancellation weighting factor corresponding to intensity values presented at the inputs; and
a data processor configured to:
process higher energy (HE) and lower energy (LE) x-ray images of a subject to obtain intensity values of pairs of corresponding aligned pixels of the HE and LE images respectively, for each of the pairs of corresponding pixels, using the intensity values of the pair as inputs to each of the first and second fitted material cancellation models to obtain corresponding first and second material cancellation weighting factors; and
creating a first dual energy (DE) x-ray image by combining the HE and LE x-ray images by log subtraction of the intensity values of the pairs of corresponding aligned pixels of the HE and LE x-ray images using the first material cancellation weighting factor corresponding to the pair of corresponding aligned pixels to yield the logarithm of a corresponding pixel value for the first DE x-ray image; and
creating a second dual energy (DE) x-ray image complementary to the first DE x-ray image by combining the HE and LE x-ray images by log subtraction of the intensity values of the pairs of corresponding aligned pixels of the HE and LE x-ray images using the second material cancellation weighting factor corresponding to the pair of corresponding aligned pixels to yield the logarithm of a corresponding pixel value for the second DE x-ray image.

21. The apparatus according to claim 20 further comprising:
first and second fitted noise cancellation models respectively corresponding to the first and second materials, each of the first and second fitted noise cancellation models comprising an input for receiving an intensity value for a pixel of the higher energy (HE) x-ray image and an input for receiving an intensity value for a pixel of the lower energy (LE) x-ray image and configured to output a noise cancellation weighting factor corresponding to intensity values presented at the inputs;
wherein the processor is further configured to:
for each of the pairs of corresponding pixels, using the intensity values of the pair as inputs to one of the first and second fitted noise cancellation models to obtain a corresponding noise cancellation weighting factor; and
processing pixels of the first DE x-ray image to reduce noise using the corresponding noise cancellation weighting factors.

* * * * *